(12) United States Patent
Miao et al.

(10) Patent No.: US 12,709,736 B2
(45) Date of Patent: Aug. 18, 2026

(54) 4D PRINTING SMART CULTURE SUBSTRATE FOR CELL GROWTH

(71) Applicant: THE GEORGE WASHINGTON UNIVERSITY, Washington, DC (US)

(72) Inventors: Shida Miao, Washington, DC (US); Haitao Cui, Washington, DC (US); Lijie Grace Zhang, Washington, DC (US)

(73) Assignee: The George Washington University, Washington, DC (US)

( * ) Notice: Subject to any disclaimer, the term of this patent is extended or adjusted under 35 U.S.C. 154(b) by 1198 days.

(21) Appl. No.: 17/690,966

(22) Filed: Mar. 9, 2022

(65) Prior Publication Data

US 2022/0204927 A1 Jun. 30, 2022

Related U.S. Application Data

(63) Continuation of application No. PCT/US2020/051598, filed on Sep. 18, 2020.
(Continued)

(51) Int. Cl.
*C12N 5/0797* (2010.01)
*B33Y 10/00* (2015.01)
(Continued)

(52) U.S. Cl.
CPC ............ *C12N 5/0623* (2013.01); *B33Y 10/00* (2014.12); *B33Y 80/00* (2014.12); *C12N 5/0062* (2013.01);
(Continued)

(58) Field of Classification Search
None
See application file for complete search history.

(56) References Cited

U.S. PATENT DOCUMENTS

2008/0262188 A1* 10/2008 Xie .................... C08G 59/5006 528/98
2010/0084784 A1 4/2010 Jabbari
(Continued)

FOREIGN PATENT DOCUMENTS

WO WO 2017-035332 3/2017

OTHER PUBLICATIONS

Cui, Haitao et al., ‘A novel near-infrared light responsive 4D printed nanoarchitecture with dynamically and remotely controllable transformation’, Nano Research, May 29, 2019, vol. 12, pp. 1381-1388.
(Continued)

*Primary Examiner* — David W Berke-Schlessel
(74) *Attorney, Agent, or Firm* — Kory D. Christensen

(57) ABSTRACT

Disclosed herein is a 4D printed programmable culture substrate with the self-morphing ability to accommodate the change in morphology of stem cells during differentiation. The 4D printed culture substrate includes a shape memory polymer that is configured for transformation from a first topographical shape to a second topographical shape during a predetermined time period in response to a stimulus, such as temperature. The first topographical shape may include micro-wells and the second topographical shape may include microgrooves, which can accommodate the growth and differentiation of neural stem cells.

20 Claims, 15 Drawing Sheets
(8 of 15 Drawing Sheet(s) Filed in Color)

Related U.S. Application Data

(60) Provisional application No. 62/903,665, filed on Sep. 20, 2019.

(51) Int. Cl.
*B33Y 80/00* (2015.01)
*C12N 5/00* (2006.01)

(52) U.S. Cl.
CPC ........ *C12N 5/0075* (2013.01); *C12N 2513/00* (2013.01); *C12N 2533/30* (2013.01); *C12N 2537/10* (2013.01); *C12N 2539/00* (2013.01)

(56) References Cited

U.S. PATENT DOCUMENTS

2015/0101325 A1* 4/2015 Beblo .................. F03G 7/0616 60/528
2016/0202244 A1 7/2016 Gobaa et al.

OTHER PUBLICATIONS

Miao, Shida et al., ‘Photolithographic-stereolithographic-tandem fabrication of 4D smart scaffolds for improved stem cell cardiomyogenic differentiation’, Biofabrication, 2018, vol. 10, article No. 035007, pp. 1-14.
Miao, Shida et al., ‘4D self-morphing culture substrate for modulating cell differentiation’, Advanced Science, Feb. 18, 2020, vol. 7, article No. 1902403, pp. 1-12.

* cited by examiner

Fix at 60°C 4
5
6
10mm

0 Min 30 Min 16 H 1 Day 2 Days 3 Days 7 Days 15 Days

Micro-Pillar Arrays

SMP Sample

Micro-Well Arrays

3D Fluorescence
3D Spectrum
Ortho (10/20)
Ortho (15/20)

Optical Images

3D Surface Plots

Day 1

Day 3

Day 7

4D PRINTING SMART CULTURE SUBSTRATE FOR CELL GROWTH

CROSS-REFERENCE TO RELATED APPLICATIONS

This application is a continuation of PCT Application No. PCT/US20/51598 filed on Sep. 18, 2020 which claims the benefit of, and priority to, U.S. Provisional Patent Application No. 62/903,665 filed on Sep. 20, 2019, the contents of which is hereby expressly incorporated by reference in its entirety.

GOVERNMENTAL RIGHTS

This invention was made with government support under MME program grant 1642186 and Director's New Innovator Award 1DP2EB020549-01 awarded by the National Institutes of Health. The government has certain rights in the invention.

FIELD

The present application relates to substrates for growing cells, and in particular the use of 4D printing for preparing substrates which may be employed for cell growth.

BACKGROUND

Neurodegenerative diseases and injuries represent an enormous burden on society, both in terms of economic cost and human suffering. Statistically, spinal cord injury occurs approximately 17,730 new cases per year, with total direct costs of treating individuals over $7 billion per year in the USA. To construct and re-establish the neurologic functions, two strategies have been conventionally applied, which are (1) to use the autograft to establish the nerve connections feasible for relatively small defects, and (2) to replace the injury region with functional scaffolds carrying regenerating axons for the regeneration of neural tissues.

Stem cell-based neural tissue engineering is a therapeutic strategy that has also been used. In this procedure, stem cell-based neural tissue not only replaces lost cells and secretes neurotrophic factors to stimulate repair and axonal growth but may also be genetically manipulated pre-implantation, thereby repairing severed axons and regaining locomotor function. Current strategies also employ three-dimensional (3D) biomimetic scaffolds with living cells to regenerate nerve tissue.

In the central nervous system (CNS), the neural stem cell (NSC) line is capable of self-renewing and differentiating into neurons and other glial cells including astrocytes and oligodendrocytes that can integrate with host tissues and repair nerve damages by improving neurogenesis and axonal growth. The undifferentiated NSCs might also repair nerves by intrinsic neuroprotective ability in which NSCs release a series of bioactive molecules, e.g., neurotrophic growth factors, immunomodulatory substances, for maintaining neural tissue homeostasis.

During the neural development in vitro, culture substrates or scaffolds, either natural or synthetic, not only provide structural and biochemical support for the monolayer or three-dimensional (3D) cultured cells but also assist in cell adhesion and cell-cell interaction. Various manufacturing methods have been used for the formation of scaffolds including electron beam lithography, photolithography, electrospinning, and printing have also been utilized for surface manufacture or modification of NSC culture substrates and scaffolds.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
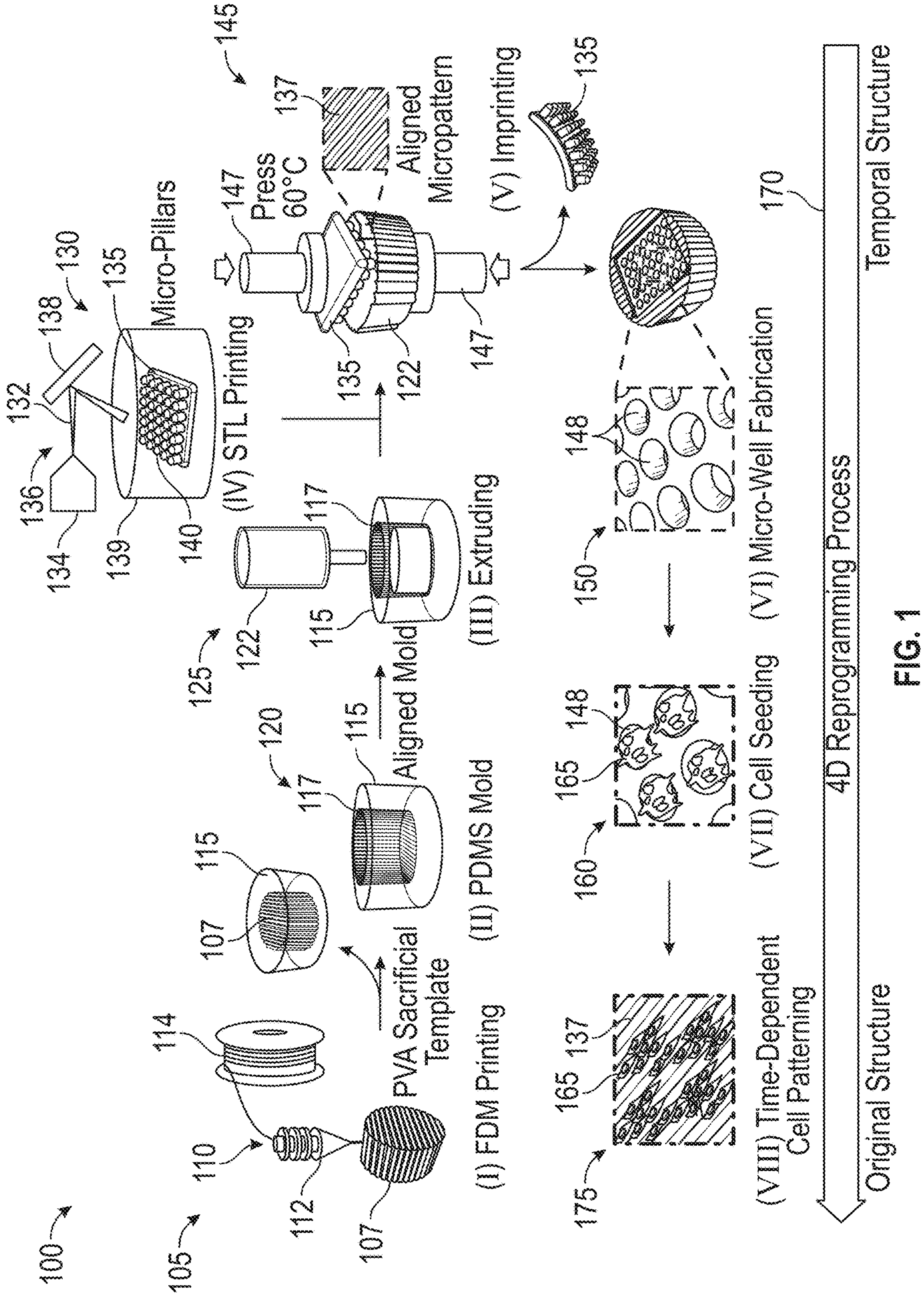
FIG. 1 is a schematic illustration of an exemplary fabrication procedure of a 4D intelligent neural substrate or scaffold with a time-dependent topographic transformation, which is used for catering desired extracellular microenvironments for NSCs development at different differentiation stages (from NSC aggregation at an early stage to highly aligned micropatterns)

Various embodiments of the disclosure are discussed in detail below. While specific implementations are discussed, it should be understood that this is done for illustration purposes only. A person skilled in the relevant art will recognize that other components and configurations may be used without departing from the spirit and scope of the disclosure.

It should be understood at the outset that although illustrative implementations of one or more embodiments are illustrated below, the disclosed apparatus and methods may be implemented using any number of techniques. The disclosure should in no way be limited to the illustrative implementations, drawings, and techniques illustrated herein, but may be modified within the scope of the appended claims along with their full scope of equivalents.

Introduction

Despite their remarkable potential, one of the major challenges in successfully utilizing stem cells for complex tissue regeneration is the difficulty in providing proper environmental cues to regulate their self-renewal and differentiation. A particular type of stem cell, namely, neural stem cells (NSCs) may be used for various neurodegenerative diseases and injuries. In the development of the adult central nervous system, NSCs dynamically appear following predetermined spatiotemporal developmental programs, and their biological characteristics greatly vary depending on the developmental stage considered. Characteristically, differentiating NSCs display significantly different morphologies and biological features at different stages, tending to aggregate at early differentiation and finally forming axonal neuron filament in late stage. This NSC differentiation typically undergoes this critical morphological changing process over the course of two weeks, including:

monolayer→aggregation→outmigration→differentiated NSCs with neurites.

Current neural scaffolds or substrates are mostly static that fail to cater to this dynamic physiological development. For instance, most of the current available techniques utilize a simple 2D or 3D microenvironment. However, there is difficulty in directing these culture systems to reflect cells' native tissue environment with dynamic physical and chemical cues.

Accordingly, disclosed herein is a 4D printed programmable culture substrate with the self-morphing ability to enhance the growth and differentiation of stem cells. The culture substrate undergoes a programmed morphing process to change from a first topographical shape to a second shape during a predetermined time period in response to a stimulus, such as temperature. For example, the topographical shape change may be from micro-wells to an aligned microgroove pattern so as to cater to the differentiation behavior of NSCs which shift from aggregates to aligned axons.

Accordingly, disclosed herein are shape memory polymers (SMPs) which may be designed to undergo the predetermined topographic shape changes. The dynamic shape transformation of the SMPs is formed by the combination of a stiff epoxy polymer, a flexible polymer and a crosslinking modulator. The relative amounts of these polymers may be modified to obtain the desired physical changes over a predetermined time at a predetermined temperature. Such predetermined time period may correspond to the growth and differentiation rate of NSCs and the predetermined temperature may be that at which such NSCs are incubated, such as about 37° C.

Accordingly, the SMPs may be initially imprinted with a permanent shape, such permanent shape being the second topographical shape. The SMPs are then deformed at a high temperature such as 60° C. to a first topographical shape and the temperature is then lowered to maintain that shape, such as from 20° C. to 25° C. The temperature is then increased to the incubation temperature such as from 35° C. to 40° C., causing the SMPs to gradually transform over about 14 days from the first topographical shape to the second topographical shape.

In order to form the culture substrate from SMP, 3D printing techniques, such as fused deposition modeling (FDM) and stereolithography (SL) may be employed along with thermomechanical reprogramming so as to fabricate the 4D programmable culture substrate.

Formation of the Culture Substrate

FIG. 1 is a schematic flow-diagram 100 illustrating a fabrication procedure of a 4D intelligent substrate with a time-dependent topographic transformation for stem cells, such as NSCs, which caters to extracellular microenvironments for NSCs development at different differentiation stages. For instance, the differentiation stages may progress from NSC aggregation at an early stage to highly aligned micropatterns. As shown in flow-diagram 100, in step 105 a sacrificial template 107 may be formed. The sacrificial template may be made up of a thermoplastic water-soluble polymer, such as polyvinyl alcohol. The sacrificial template may be generally cylindrical or have other polygonal shape, and may be formed with a topographical shape, such as a micropattern on its external surface, such as microgrooves. The microgrooves may be aligned across one or more surfaces, one or more of the top or bottom, or sides or side surface so as to impose a corresponding pattern to the substrate. Other shapes may be used in addition to microgrooves, such as circles, ovals, rectangles, squares, or other polygonal shapes, and which selection may depend on the cells or stem cells employed for growth, and the initial shapes required for such cells.

The sacrificial template may be formed by the use of 3D fused deposition modeling (FDM) 110. In FDM a continuous filament of the polymer is drawn from a spool 114 and ejected through a heated nozzle 112 which moves under computer control depositing thin layers to form a printed shape, in this case the sacrificial template 107. The nozzle is moved according to predetermined design. Example FDM printers include Solidoodle® 3D FDM printer which may be controlled with open source software such as Pronterface® software.

The sacrificial template 107 may be coated in a mold material 115 which is non water-soluble, such as polydimethylsiloxane (PDMS). The mold material 115 may then be cured, which may be carried out with the use of a curing agent and with exposure to heat. The curing may be carried out a temperature sufficient for curing, and which may be at least 60° C., at least 65° C., or at least 70° C. The sacrificial template 107 may then be removed by the application of water, increased heat, and/or perturbation techniques such as sonication. With the removal of the sacrificial template 107, the mold material 115 is finally formed in step 120. Due to the coupling of the sacrificial template with the mold material microgrooves are formed on an internal chamber 117 of the mold material 115 corresponding to the microgrooves in the sacrificial template 107.

The microgrooves in the mold material 115 and sacrificial template 107 may have a plurality of microgrooves across their outer surfaces. These microgrooves may be sized to facilitate the change in morphology of stem cells, and in particular NSCs. The microgrooves may be shaped according to a final morphology after or along an advanced state of differentiation of the stem cells. The microgrooves maybe longitudinal and linear, and may be substantially parallel, and may be narrower than micro-wells. The microgrooves may have a shape that is not enclosed on all sides, but may extend linearly. The microgrooves may have a width of for example, of from 10 μm to 500 μm, or alternatively from 25 to 400 or alternatively from 50 to 300 or alternatively from 75 to 200 or alternatively from 75 to 125 or alternatively at least 50 or alternatively at least 100 or alternatively at least 150 and combinations of the aforementioned.

After preparation of the mold material 115, the culture substrate 122 may be formed by extruding the SMP into the PDMS mold in step 125, which may be cured at an increased temperature as described herein. Microgrooves are formed on the surface of the culture substrate 122 corresponding to the microgrooves in the internal chamber 117 of the mold material 115, thereby forming a first topographical shape in the culture substrate 122 and which is also the permanent shape. Although microgrooves are used in the present example, any shape may be imprinted on the culture substrate 122, such shape first formed on the mold material 115 and then correspondingly formed by extrusion or other imprinting method onto the culture substrate 122. Such other shapes may be used in addition to microgrooves, such as circles, ovals, rectangles, squares, or other polygonal shapes, and which selection may depend on the cells or stem cells employed for growth, and the initial shapes required for such cells.

In order to form micro-wells in the culture substrate 122 a micropillar template 135 with a plurality of micropillars 140 may be prepared in step 130 employing stereolithography (STL) 3D printing. Materials such as polymers harder than the culture substrate 122 may be used, for example polymers having esters of acrylic acid, such as polymethyl methacrylate (PMMA). The STL 3D printing apparatus 136 may include a laser source 134 from which a laser beam 132 into a container 139 having a platform and UV curable resin. The platform is computer controlled to move in predetermined directions such that the laser beam contacts and cures the resin, thereby layer by layer forming the culture substrate 122. Any commercially available STL 3D printing apparatus may be employed including desktop STL printer, along with software controls such as Autodesk 123D.

The micropillar template 135 may be used to form micro-wells in the culture substrate 122 as in step 145. A press, 147 such as a clamp, may be used to press the micropillar template 135 against the culture substrate 122 such that the plurality of micropillars 140 form corresponding micro-wells into the culture substrate 122. The surface of culture substrate 122 in which the micro-wells will be formed includes a micropattern 137, namely the plurality of aligned microgrooves formed in the extrusion of step 125. The mechanical pressing may be carried out in heat such that the culture substrate 122 is softened to allow for the imprinting of the micro-well design, and the subsequently cooled or moved to ice water to set the design in place, for example for 10 minutes. This may be referred to as thermomechanical reprogramming. The culture substrate 122 with the micro-wells formed shown in step 150 has a plurality of micro-wells 148 formed in its surface.

The plurality of micropillars 140 formed in the micropillar template 135 may be sized to form micro-wells in the culture substrate 122 to facilitate growth in the initial phases of stem cell growth and differentiation, including that particular for NCSs. The shape of the micro-wells may be substantially circular or oval, or may be square, rectangular or other polygonal shape and may be enclosed on all sides, and wider and rounder than the aforementioned micro-grooves to accommodate aggregates of cells. For instance, when circular, the diameters of the micropillars and the corresponding micro-wells 148 may have a diameter of from 50 to 2000 μm, alternatively from 200 to 1500 μm, alternatively from 300 to 1000 μm (1 mm), alternatively from 400 to 800 μm, and combinations thereof. Other sizes may be employed for obtaining desired growth of stem cells or other cells. Such micro-wells are a second topographical shape on the surface of the substrate 122. Although micro-wells are employed as the second topographical shape in this example, any other shapes may be used which may correspond to that required for NSCs or stem cells other than NSCs.

As shown in step 160 the culture substrate 122 may then be seeded with stem cells 165, which are in this case NSCs. In the initial stages of the growth, the NSCs are in aggregate form, and so the shape of the micro-well structure on the culture substrate 122 facilitates growth. As discussed since NSCs are initially in aggregate form, a microwell topographical shape as the first topographical shape accommodates the initial shape of NSCs as they grow and differentiate. Over a predetermined timeframe at a predetermined temperature, the shape of the culture substrate 122 changes. The first topographical shape includes the plurality of micro-wells 148. As time progresses, shown by arrow 170, due to the culture substrate 122 being made up of SMPs, the shape of the culture substrate 122 changes, such that the micro-wells transition to aligned microgroove shapes, which may be the second topographical shape or permanent shape, as in step 175. The change in shape facilitates the growth and change in the morphology of NSCs as they progress through differentiation. The NSCs start out as aggregates, but then as growth continues, their morphology changes into a more linear shape. Accordingly, as they NSCs transition from aggregates toward NSCs with neurites, the culture substrate 122 correspondingly changes shape from circular, to the aligned micropattern 137 having aligned microgrooves. The aligned micropattern 137 may be considered the second topographic shape, or permanent shape.

As disclosed herein, each of the first and second topographical shapes may include cell receiving portions which may stably contain cells, including stem cells and NSC's, and hold cell growth media. Accordingly, the first and second topographical shapes may include depressions, impressions, apertures or indents in whatever shape so as to hold and contain such cells and support their growth. While in this case the culture substrate 122 is employed to transition from micro-wells to the aligned micropattern, in other embodiments, the first and second topographical shapes may be reversed, or alternatively, other initial or final shapes may be employed, including square, polygonal, circular, aligned. The surfaces of the substrate and the and second topographical shapes permit attachment and adherence of the cells and stem cells disclosed herein.

Shape Memory Polymers

The SMPs herein change shape over a predetermined period of time at a predetermined temperature. The composition can be adjusted to accommodate any predetermined time period to facilitate growth of the particular cells selected for growth, such as NSCs. The first predetermined shape may be the temporary shape of the SMP composition, while the second shape may be a permanent shape. Over the period of time, the SMP composition, which may be formed into a culture substrate for growth of cells, has a topography that dynamically changes from the first temporary shape back to the second permanent shape, or in other words, from a first topographical shape to a second topographical shape. The time period for the change in shape may be selected based on the rate at which the selected cells grow and/or differentiate.

Chemical crosslinks in the SMPs may be utilized to set the permanent shape, while the transition temperature ($T_{trans}$), typically referring the glass transition temperature (Tg), may be used to control the molecular switching segments for achieving the temporary shape.

Figure 2:
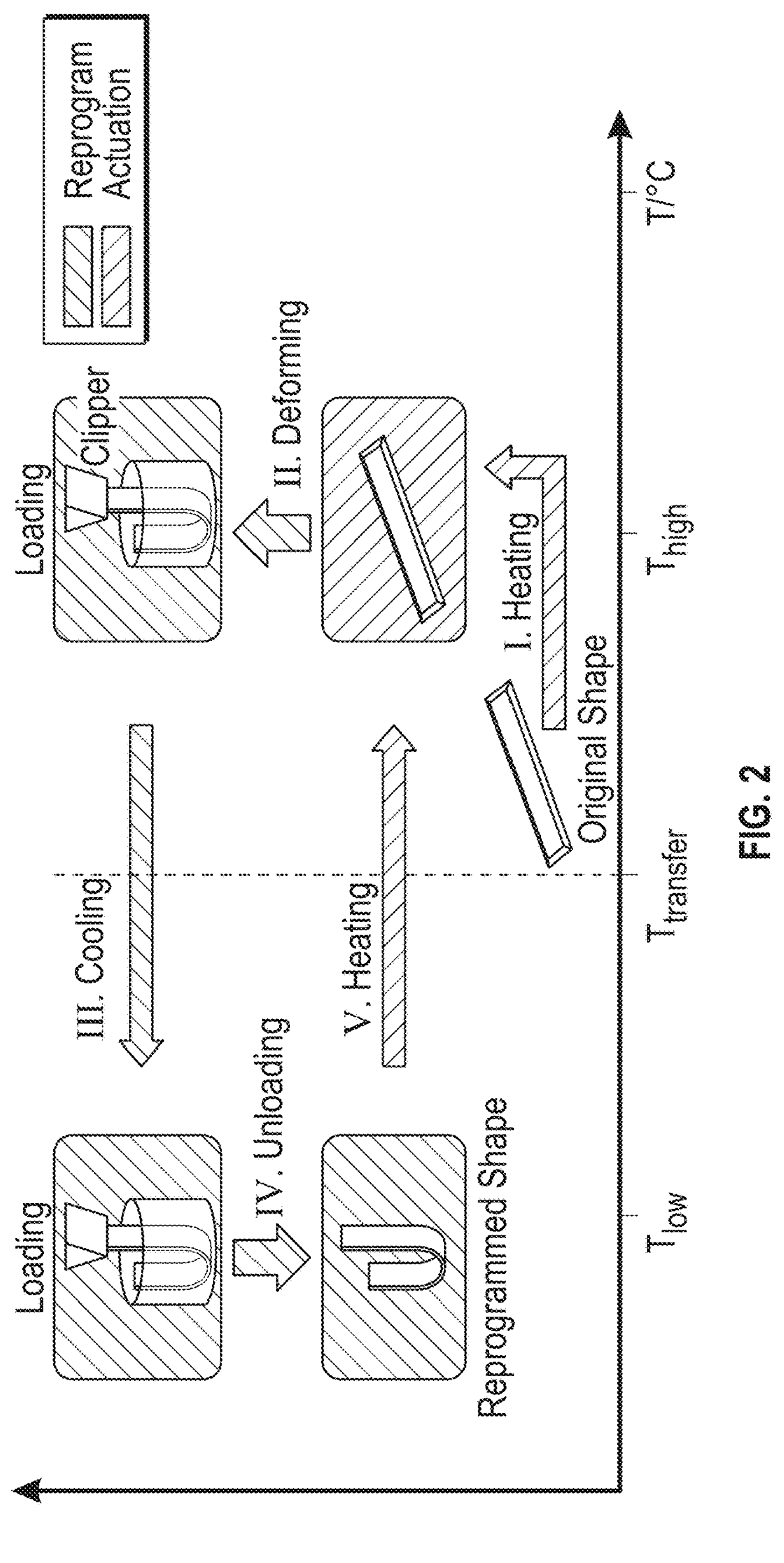
FIG. 2 is a flow diagram of the process of shape memory effect, including I, increasing the temperature over transition temperature; II, exerting a U shape change with enforced restriction; III, fixing a temporary U shape at a lower temperature; IV, removing externally enforced restriction; V, increasing the temperature to recover the original shape.

FIG. 2 illustrates the shape memory properties of the SMPs herein. As shown in step I, the SMPs in a permanent shape are heated above their $T_{trans}$, and as shown in step II, the molecular switching segments are "softened" and deformation can be exerted to set the temporary shape, in this case the shape of a clipper. This temporary shape may may be considered the second topographical shape, whereas the original permanent flat planar shape may be considered the second topographical shape. As shown in step III, as the temperature is decreased below the $T_{trans}$, the molecular switching segments will "freeze" to immobilize the predesigned temporary shape shown in step IV even in the absence of a load. As shown in step V, the SMPs then can recover their permanent shape (thereby shifting from the first temporary topographical shape to the second permanent topographical shape) upon returning to a temperature over $T_{trans}$ since the molecular switching segments are softened again, allowing the crosslink networks to revert the structure to the original shape.

During this shape changing process of the SMPs, the chemical structure of the polymer determines the $T_{trans}$ and transformation rate ($T_{rate}$). Specifically, an appropriate ratio of stiff chemical groups and flexible chain, and moderate crosslinking density are selected to meet various demand for different $T_{trans}$ and $T_{rate}$ (which depend on the needs of the selected cells for growth). For example, based on the understanding of neural development, for NSCs, it is expected that the ideal culture substrate should perform a two-week dynamic shape transformation at about 37° C. (physiological temperature or cell culture temperature) to cater the NSC differentiation behavior. Thus, by manipulating the components and the processing parameters of the SMPs, the shape memory properties of the synthesized materials can be tuned to obtain an optimized or ideal morphing process.

As mentioned, the SMPs are made up of a combination of a stiff monomer, a flexible cross-linker or chain, and a crosslinking modulator.

The stiff monomer or chemical groups may be any monomer which provide stiffness or tensile strength to a polymer composition. Exemplary stiff monomers include epoxies. Exemplary epoxies may include bisphenol epoxides, aromatic diepoxides, diglycidyl ethers, and which may include one or two phenyl rings per monomer, and/or may include two or more epoxy groups per monomer. A particular epoxy includes bisphenol A diglycidyl ether (BPADGE).

The flexible cross-linker may be selected based on the chemistry of the stiff monomer and/or the crosslinking modulator. The flexible cross-linker may be a flexible aliphatic crosslinker. The crosslinker may be a mono-, di-, or poly-amine, and may include one or two terminal amine functional groups. The aliphatic cross-linker may include a polyether backbone, which may include for instance ethylene oxide, propylene oxide, or a mixture thereof. A particular exemplary flexible cross-linker includes ((poly(propylene glycol) bis(2-aminopropyl) ether (which may also be referred to as polyoxypropylenediamine).

The crosslinking modulator may be selected based on the chemistry of the stiff monomer and/or the flexible cross-linker. The modulator may be an amine, including alkyl amines with one, two or more amine groups, with one or two terminal amino groups. The amines may be primary, secondary or tertiary amines. The alkyl amine may have a hydrocarbon base chain which may be saturated or unsaturated, straight or branched, including $C_1$-$C_{20}$ alkyl, or $C_5$-$C_{15}$ alkyl, $C_7$-$C_{12}$, or $C_9$-$C_{11}$ alkyl, or $C_{10}$ alkyl, or combinations of the aforementioned. Particular alkyl amines include octanamine, nonanamine, decanamine (also referred to as decylamine), undecanamine, dodecanamine, where the amine is in the first position.

Figure 3:
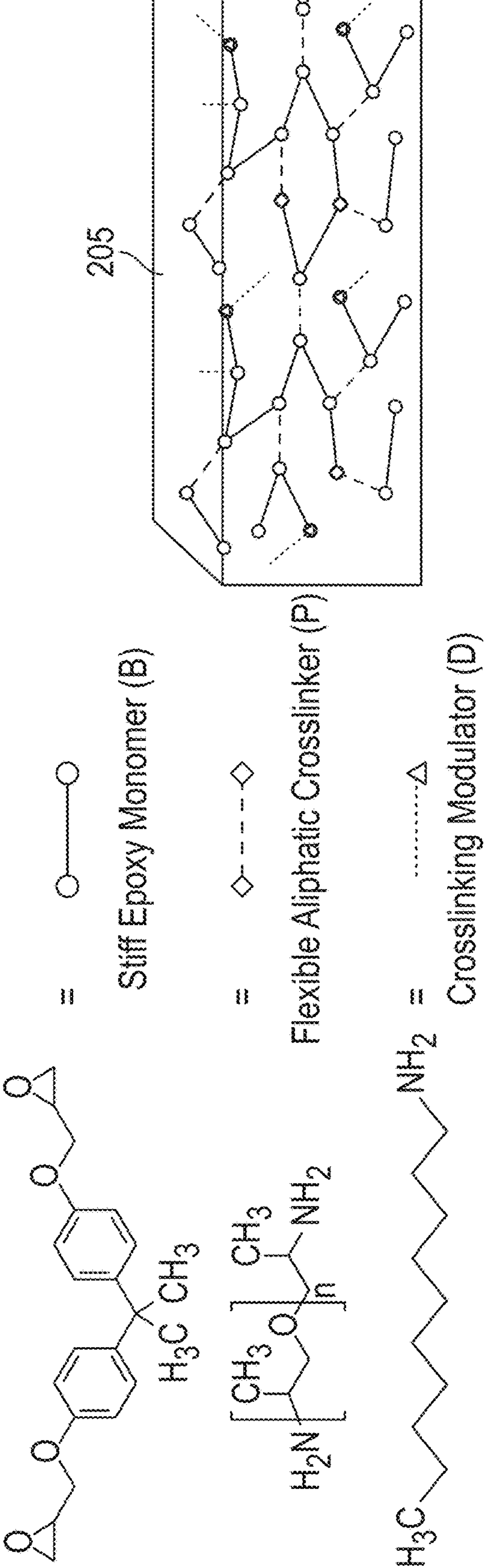
FIG. 3 illustrates the synthesis and characterization of synthesized polymeric materials, including the chemical structure of shape memory polymers (SMPs) including stiff epoxy monomer (B), flexible aliphatic crosslinker (P) and crosslinking modulator (D)

While any combination of the above stiff monomer, flexible cross-linker, and crosslinking modulator may be employed, an exemplary combination of monomers to make up the SMPs as the 4D component of the culture substrate includes bisphenol A diglycidyl ether (referred to herein also as "B"), ((poly(propylene glycol) bis(2-aminopropyl) ether (referred to herein also as "P"), and decylamine ether (referred to herein also as "D"). FIG. 3 illustrates these particular selected monomer components together which form an exemplary SMP composition 205. While these monomers are shown SMP composition 205, any combination of the mentioned monomer, flexible cross-linker, and crosslinking modulator may be employed, and tuned for the particular temperature and selected cells.

While any methodology may be employed to form the SMP, to facilitate the preparation of the SMP, one of the components may be held constant while varying the ratios of the remaining components. For instance, the stiff monomer may be held constant, while the amounts of the flexible cross-linker and crosslinking modulator are varied. While limited to any particular range, and the particular amounts may depend on the particular monomers selected. While maintaining the stiff monomer constant, the ratios of the flexible monomer to crosslinking modulator, on a molar basis, may range from 2:1 to 1:8, or alternatively from 3:4 to 1:3, with a particular ratio including 11:18. Together, the ratios of stiff monomer: flexible crosslinker: crosslinking modulator may range from 5:2:1 to 10:1:8, or alternatively from 10:3:4 to 5:1:3, with a particular ratio including 40:11:18.

Accordingly, the rate at which the SMPs change shape, and therefore the relative amounts of the components making up the SMPs, may be selected based on the rate at which the chosen cells grow and differentiate at a predetermined temperature. The temperature at which the second shape is set may be referred to as the fixing temperature, and the temperature at which the SMP transitions back to the first shape (i.e., the original shape) may be referred to as the recovery temperature. The fixing temperature may be below the $T_g$ (or $T_{trans}$) and the recovery temperature may be at a temperature above the $T_g$ ($T_{trans}$). The rate at which the SMP transitions back to the first shape may depend on how far above the recovery temperature is above the SMP's $T_g$.

After imprinting the permanent second topographical shape, the SMPs may be deformed to the first topographical shape at a deformation fixing temperature which will be a high temperature, sufficiently high to permit deformation and which may also be above the recovery temperature, such as for example, at least 50° C., alternatively at least 55° C., alternatively at least 60° C., alternatively at least 65° C., alternatively at least 70° C. or more. The temperature can then be decreased to the fixing temperature to set the first topographical shape which may be a low temperature, which may be lower than the recovery temperature at which transformation occurs, for example, from 20° C. to 30° C., alternatively from 20° C. to 30° C., alternatively from 22° C. to 25° C., and may be for example about 23° C., or room temperature. The temperature may then be changed from the fixing temperature to the recovery temperature, which is the temperature at which the SMP gradually transforms to the first topographic shape, and may correspond to the culture temperature for the particular stem cells such as NSCs, the recovery temperature being for example from about 31° C. to about 45° C., alternatively from about 33° C. to about 40° C., alternatively from about 35° C. to about 39° C., alternatively about 37° C. These temperatures may vary based on the cells employed, as well as the culture media, as well as other factors.

Accordingly, the temperature may be the stimulus for causing the transformation from a first topographical shape to a second topographical shape, but however, other stimuli may be employed, such as pressure, electrical charge, light, added chemicals, or other.

Figure 4:
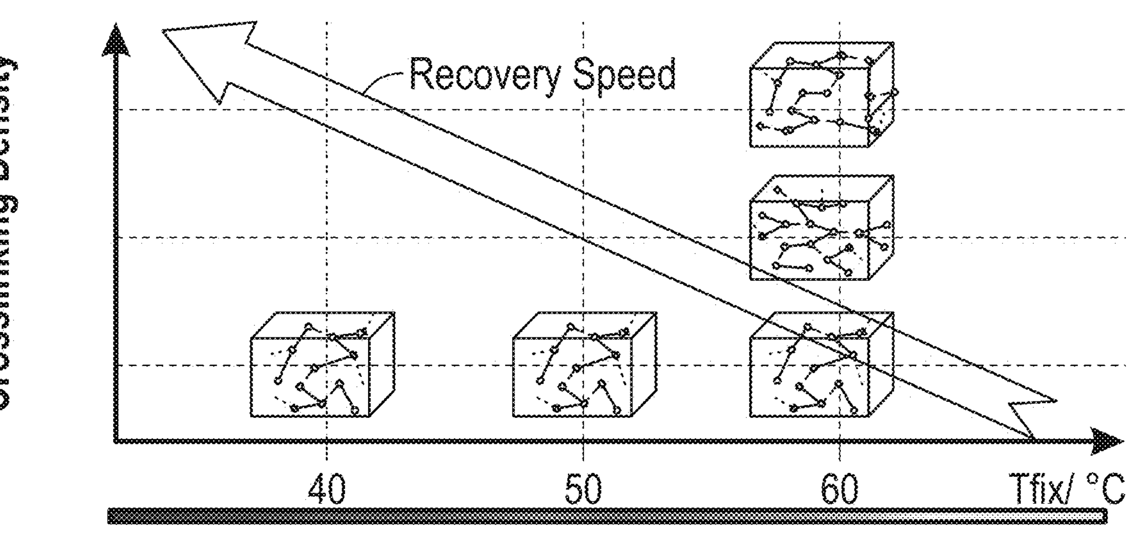
FIG. 4 is a graph illustrating the recovery speed of shape memory polymers when varying the fixing temperature and cross-linking density.

The relative amounts of the components of the SMP composition may be adjusted such that the $T_g$ and crosslinking density are correspondingly adjusted to achieve the predetermined shape change over the predetermined time period at the predetermined temperature. In particular, the recovery or transition of the SMPs may be determined by the switching phase. For instance, as shown in FIG. 4, compositions with lower $T_g$ and higher crosslinking density contribute to a faster recovery speed. A lower $T_g$ is softer at recovery temperature, which leads to faster shape recovery. Whereas a higher crosslinking density increases the responsive efficiency of the switching phase.

As disclosed herein, depending on the cells employed, the time for recovery from the temporary shape (first topographical shape) to the original permanent shape (second topographical shape) may range from 3 minutes to 6 months, alternatively from 12 hours to 4 months, alternatively from 1 to 30 days, alternatively from 2 to 20 days, alternatively from 3 to 17 days, alternatively from 3 to 15 days, alternatively about 14 days, which may depend on the cell type, temperature, and initial and final shapes.

As disclosed herein, the composition of the SMPs may be adjusted such that the shape of the SMPs may change from a first predetermined shape to a second predetermined shape over a fourteen-day time period at a temperature of about 37° C.

Cells for Culture Substrate

Any cells may be employed with the 4D culture substrate herein which respond to shape and topographical cues during growth or differentiation. Particular cells include stem cells, adherent stem cells, including undifferentiated or partially differentiated cells. Particular cells for use herein include NSCs which include any cells which can differentiate into neurons or neural cells, and which include neural progenitor cells. The NSCs herein include pluripotent, multipotent stem cells, embryonic stem cells, and adult stem cells, mesenchymal stem cells, endothelial progenitor cells (which maybe isolated from bone marrow or peripheral blood), or any cells which are capable of differentiating into neurons or neural cells. NSCs herein include cells having the ability to continually proliferate in the undifferentiated state and the ability to differentiate into various neurons and glia from one stem cell. The neurons herein include neurites which may refer to any projection from the neuron cell body, including axons and dendrites. The NSCs herein can be from any animal or mammal including human, mouse, cows, pigs, sheep, horses, rats, dogs, cats, and the like, and may be obtained from a neuroectoderm of any of the aforementioned animals or mammals. The adherent stem cells may adhere to the surfaces of the substrate, and in particular to the material making up the surfaces of the substrate, including plastic and polymers disclosed herein.

The 4D culture substrate disclosed herein caters to the extracellular microenvironments for stem cells such as NSCs for their development at different differentiation stages, from NSC aggregation at an early stage to highly aligned micropatterns. In the initial stages of development, NSCs are in aggregate form and so benefit from a micro-well cell culture shape as described above. AS the NSCs develop into Neurons, neurites extend from the cell body and benefit from the more aligned shape of the culture substrate as it transitions to a more aligned microgroove shape.

The cells may be cultured on the culture substrate including the micro-wells at a density of from $1\times10^2$ to $1\times10^8$, alternatively from $1\times10^3$ to $1\times10^7$, alternatively from $1\times10^4$ to $1\times10^5$, alternatively from $1\times10^4$ to $1\times10^5$ in cells/mL, and combinations of the aforementioned and particular densities include $1\times10^4$, $3.3\times10^4$, $1\times10^5$ cells/mL.

The neurites extending from the neurons may extend along the axis of the microgrooves of the culture substrate disclosed herein which are present in the second shape configuration. The neurons may extend at an angle of +/−30 degrees or less from the axis of the microgrooves, or alternatively +/−20 degrees or less, alternatively +/−15 degrees or less, or alternative +/−10 degrees or less, or alternative +/−5 degrees or less, or alternative +/−2 degrees or less, or about 0 degrees, being substantially completely aligned.

EXAMPLES

Five samples were first developed as shown in Table 1 below.

TABLE 1

The components and formulae of the synthesized polymeric materials.

| No | Sample Code | Bisphenol diglycidyl A ether (B) /g | Bisphenol diglycidyl A ether (B) /mol | poly(propylene glycol) bis(2-aminopropyl) ether (P) /g | poly(propylene glycol) bis(2-aminopropyl) ether (P) /mol | Decylamine (D) /g | Decylamine (D) /mol |
|---|---|---|---|---|---|---|---|
| 1 | BP500D000 | 3.40 | 0.010 | 1.15 | 0.00500 | 0.00 | 0.00000 |
| 2 | BP400D200 | 3.40 | 0.010 | 0.92 | 0.00400 | 0.33 | 0.00200 |
| 3 | BP300D400 | 3.40 | 0.010 | 0.69 | 0.00300 | 0.66 | 0.00400 |
| 4 | BP200D600 | 3.40 | 0.010 | 0.46 | 0.00200 | 0.99 | 0.00600 |
| 5 | BP100D800 | 3.40 | 0.010 | 0.23 | 0.00100 | 1.32 | 0.00800 |
| 6 | BP275D450 | 3.40 | 0.010 | 0.63 | 0.00275 | 0.75 | 0.00450 |
| 7 | BP250D500 | 3.40 | 0.010 | 0.58 | 0.00250 | 0.83 | 0.00500 |
| 8 | BP225D550 | 3.40 | 0.010 | 0.52 | 0.00225 | 0.91 | 0.00550 |

In the design, the stiff epoxy monomer (bisphenol A diglycidyl ether) was kept constant, while the ratio of flexible aliphatic crosslinker ((poly(propylene glycol) bis(2-aminopropyl) ether) or crosslinking modulator (decylamine) was changed to adjust crosslinking density. Poly(propylene glycol) bis(2-aminopropyl ether), bisphenol A diglycidyl ether, and decylamine were mixed homogeneously in a glass beaker at room temperature. The mixture was then centrifuged at 1500 rpm for 3 min to remove bubbles. The ratio of the components was varied to determine the properties of the final constructs. The 4D ink was precured at 100° C. for 1.5 h, and finally cured at 135° C. for another 1.5 h.

To perform shape transformation at 37° C., the sample with the Tg around 37° C. was particularly designed, so that the fixing temperature and the recovery temperature was set below and above 37° C., respectively. Among these samples, BP300D400, BP200D600, and PB100D800 showed a Tg at 46° C., 40° C., and 25° C., respectively.

Figure 5:
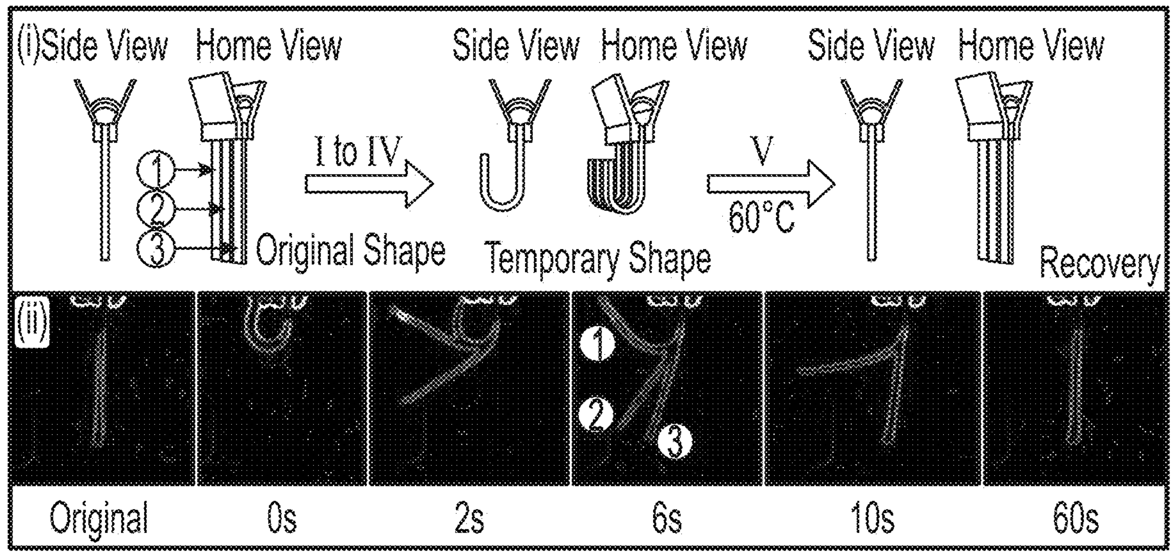
FIG. 5 illustrates Shape recovery of the synthesized materials ①BP300D400, ②BP200D600, and ③BP100D800, including (i) the immobilization of the three samples which are treated with same conditions, and (ii) Shape recovery process of V recorded from side view, displaying the different recovery speeds of the three materials, and wherein all the samples were bent to U shape at 60° C. and fixed a temporary shape at 23° C., and the shape recovery performed at 60° C.

All of these samples were able to be softened and deformed into a U shape at ~60° C., and could be fixed a temporary shape at room temperature (~avg. 23° C.), as shown in FIG. 5 part (i), with steps I to IV and V corresponding to the steps in FIG. 2. FIG. 5 part (ii) illustrates the shape recovery process of step V recorded from side view, displaying the different recovery speeds of the three materials. All the samples were bent to U shape at 60° C. and fixed a temporary shape at 23° C. The shape recovery performed at 60° C. As shown in FIG. 5 part (ii), the samples displayed different $T_{rate}$ at 60° C. in their recovery processes, due to their different Tg and crosslinking density. This confirms that the sample with a lower Tg and a higher cross-linking density contributes to a faster recovery speed.

Figures 6A, 6B:
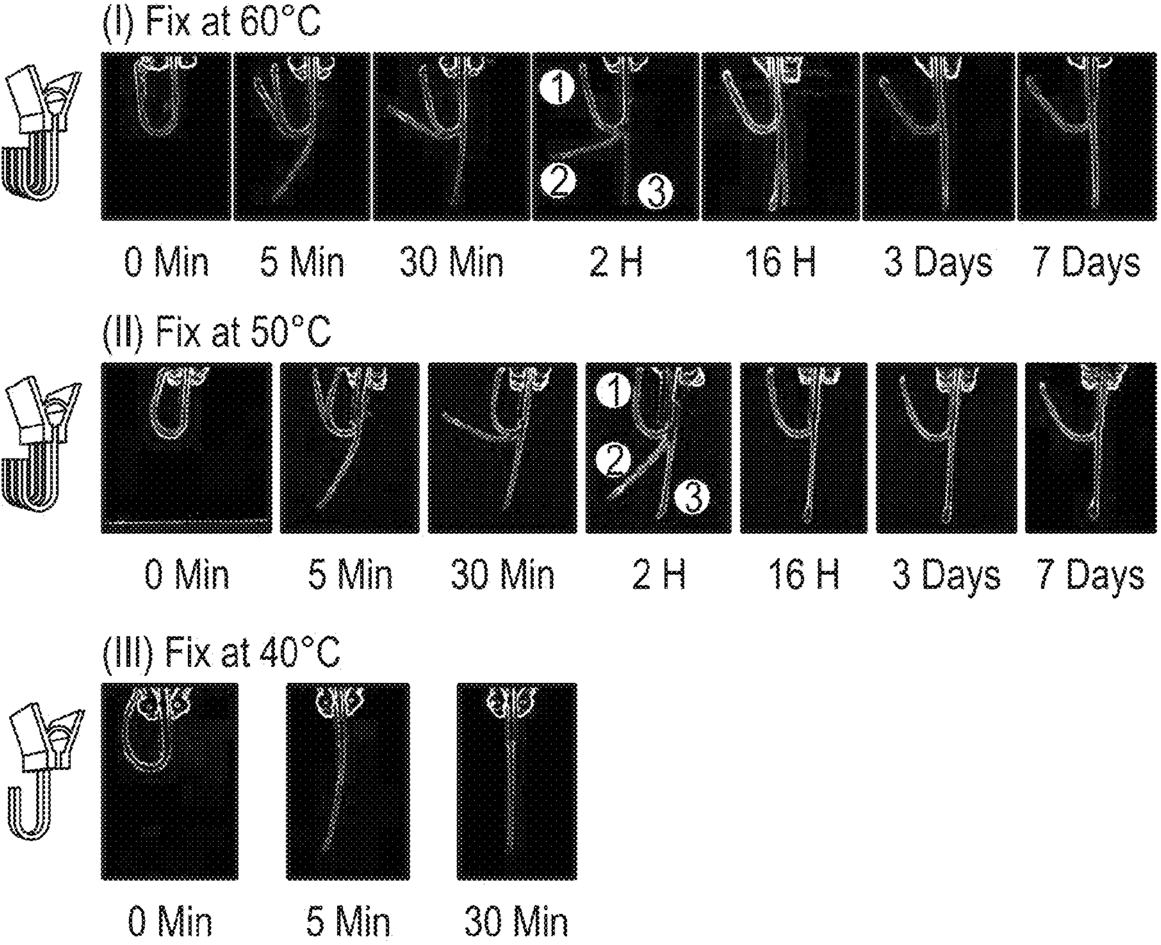
FIG. 6A illustrates the shape recovery process of shape memory polymers ①Sample BP300D400; ②Sample BP200D600; ③Sample BP100D800, displaying the different recovery speeds at different fixing temperatures, where (I) fixing the temporary shape at 60° C. and recovering at 37° C., (II) fixing at 50° C. and recovering at 37° C., and (III) fixing at 40° C. and recovering at 37° C.
FIG. 6B illustrates the shape recovery process of shape memory polymers ④Sample BP275D450; ⑤Sample BP250D500; ⑥Sample BP225D550, which were fixed at 60° C. and recovered at 37° C.

Although these samples demonstrated a typical shape recovery process, they cannot be directly used as cell culture matrices to cater the NSCs differentiation behaviors, due to the high recovery temperature and the fast recovery speeds. Therefore, the recovery behavior of these samples was further investigated at 37° C., with the results shown in FIGS. 6A-B. FIGS. 6A-B illustrates the recovery speed of shape memory polymers when varying the deformation temperature and cross-linking density, with FIG. 6A showing the shape recovery process of shape memory polymers ①Sample BP300D400; ②Sample BP200D600; ③Sample BP100D800. These display the different recovery speeds at different deformation temperatures, with part (I) deforming the temporary shape at 60° C. and recovering at 37° C., part (II) deforming at 50° C. and recovering at 37° C., and part (III) deforming at 40° C. and recovering at 37° C.

As expected, all these samples exhibited significantly slower recovery speed than that at 60° C., as shown in FIG.

6A part (I). BP200D600 and BP100D800 fully recovered at three days, while BP300D400 could not completely recover at 15 days. For the neural development study, BP300D400 is too slow while BP200D600 is too fast. Additionally, another factor that influences recovery speed is the deformation temperature. Referring back to FIG. 4, the switching segments in the SMP are much stiffer at a lower temperature, so that it stores more energy during deformation, leading to faster shape recovery. When the samples were deformed at 50° C., the recovery speeds of samples were faster, as illustrated in FIG. 6A part (II). Moreover, when the deformation was at 40° C., only BP100D800 fully recovered within 30 min, but BP300D400 and BP200D600 were too stubborn to deform due to their high $T_{gs}$, as shown in FIG. 6A part (III). From these results, it can be concluded that the effect of ink formulation or chemical structure is much higher than that of deformation temperature. Three more samples were further developed as listed in the last three rows in Table I, where the ratio of stiff and soft monomers was ranged from 3:4 (BP300D400) to 1:3 (BP200D600) based on the previous results in FIG. 6A.

FIG. 6B illustrates the shape recovery process of shape memory polymers ④Sample BP275D450; ⑤Sample BP250D500; ⑥Sample BP225D550, which were deformed at 60° C. and recovered at 37° C. As illustrated in FIG. 6B, BP275D450 showed a maximum 2-weeks recovery duration while BP250D500 and BP225D550 fully recovered within two days. From this data, it was determined that BP275D450 could provide appropriate time for NSC aggregation and the following outmigration. Moreover, the actual transformation time of BP275D450 can also be controlled by changing the deformation degree or pattern to obtain a faster recovery speed (from 3 days to 15 days).

Figure 7A:
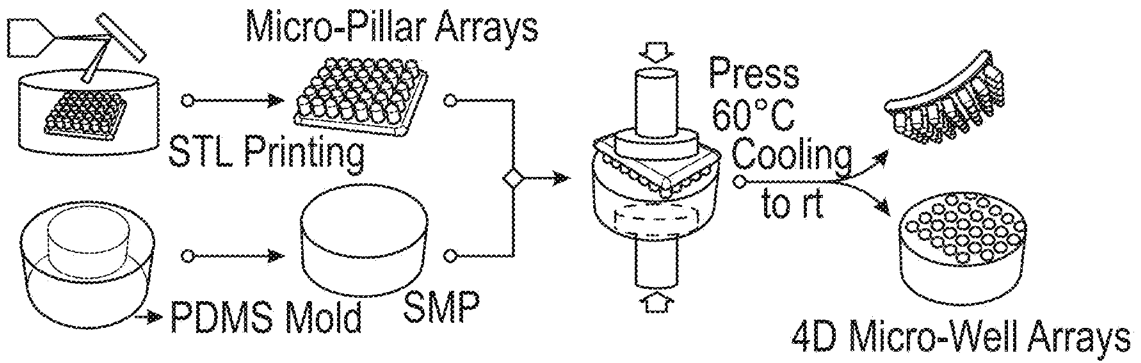
FIG. 7A illustrates a flow diagram with illustration of the fabrication of micro-well arrays.
Figure 7B:
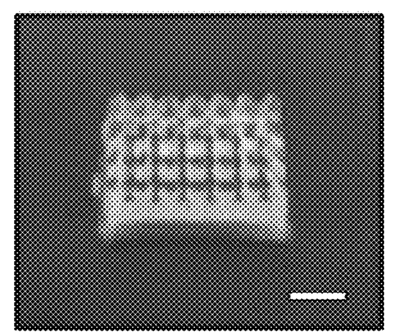
FIG. 7B illustrates photo images of stereolithography printed micro-pillar arrays with 800×800 μm pillar size (Scale bar, 2.5 mm), SMP sample (Scale bar, 5 mm), and 4D micro-well arrays with 800×800 μm well size (Scale bar, 5 mm)
Figure 7B:
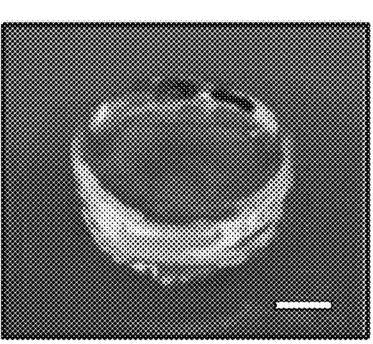
Figure 7B:
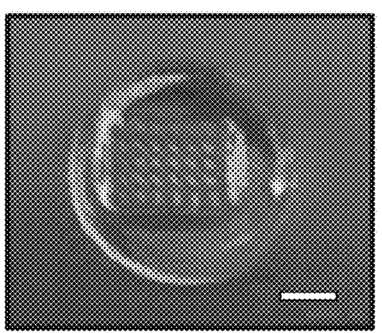
Figure 7C:
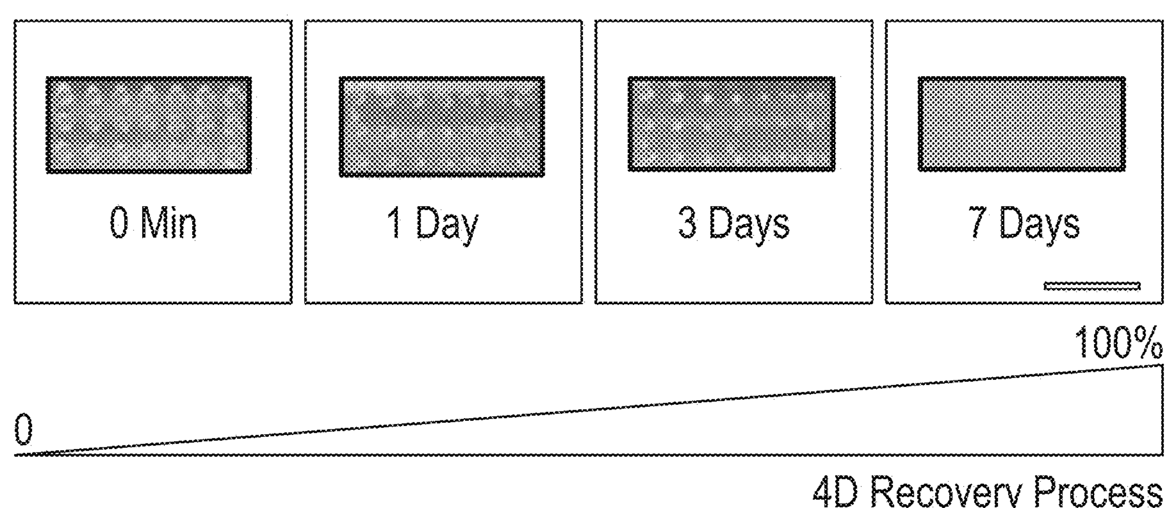
FIG. 7C illustrates a Shape transformation process from micro-well to flat with the sample having an 800×800 μm well size, showing that when incubated in 37° C., the micro-well arrays were gradually transformed, which still visible at three days, and almost restored its original flat surface after seven days.
Figure 7D:
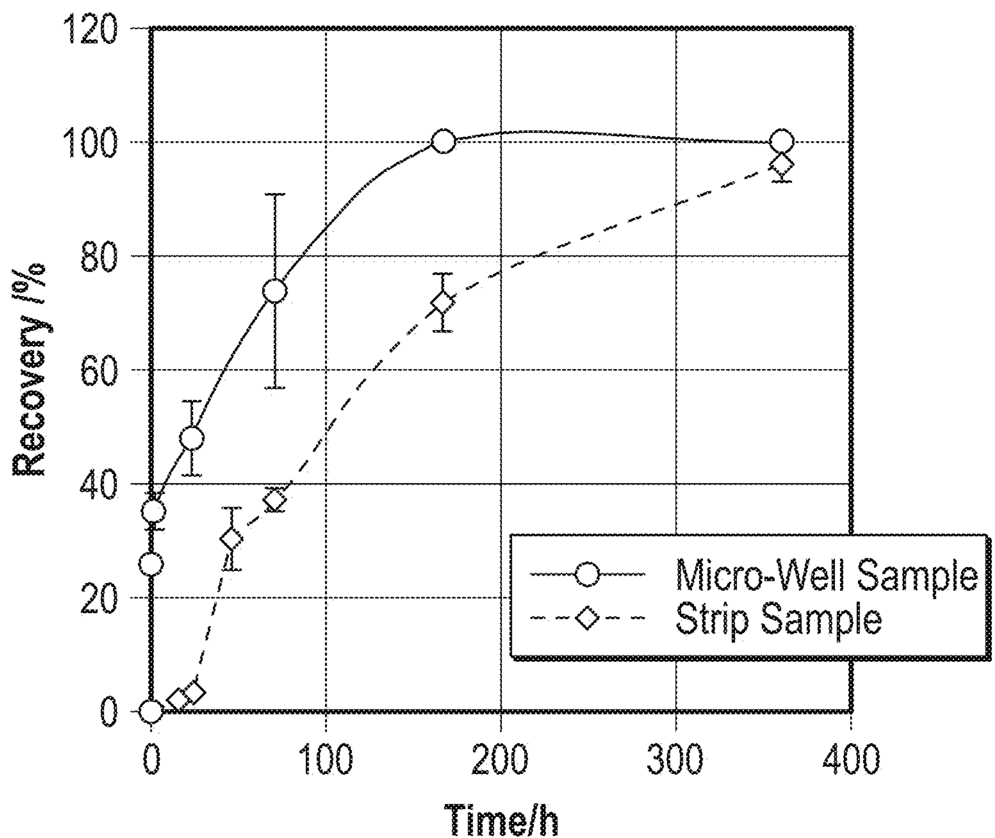
FIG. 7D is a graph illustrating the dynamic recovery process of the strip sample and micro-well array demonstrated by the relation between recovery degree and incubation time.

To investigate the transformative ability of pattern for promoting the NSC aggregation, the shape recovery properties of BP275D450 from micro-well to flat surface was determined. As shown in FIGS. 7A and 7B, micro-well arrays were created using the SMP samples by imprinting SL-printed micro-pillar PMMA arrays via the thermomechanical reprogramming process. Since PMMA has a much higher Tg (~105° C.) than BP275D450, micro-well arrays were generated after imprinting at 60° C., and the temporary micro-well arrays were immediately fixed after cooling to room temperature. The shape transformation process from micro-well to flat was demonstrated as shown in FIG. 7C with the sample having an 800×800 μm well size. When incubated at 37° C., the micro-well arrays were gradually transformed, which still visible at three days, and almost restored its original flat surface after seven days. The dynamic recovery process of the strip sample and micro-well arrays were compared in FIG. 7D. In FIG. 7D. The dynamic recovery process of the strip sample and micro-well array sample demonstrated by the relation between recovery degree and incubation time. The micro-well arrays showed a faster recovery speed than strip samples, which might be owing to the higher energy storage or lower deformation degree during micro-well deformation. Taking the sample fidelity and operation accessibility into consideration, all the 4D culture substrates were prepared with a thickness of 6 mm to generate the micro-well arrays with a depth up to a maximum of 800 μm.

Figures 8A, 8B, 8C:
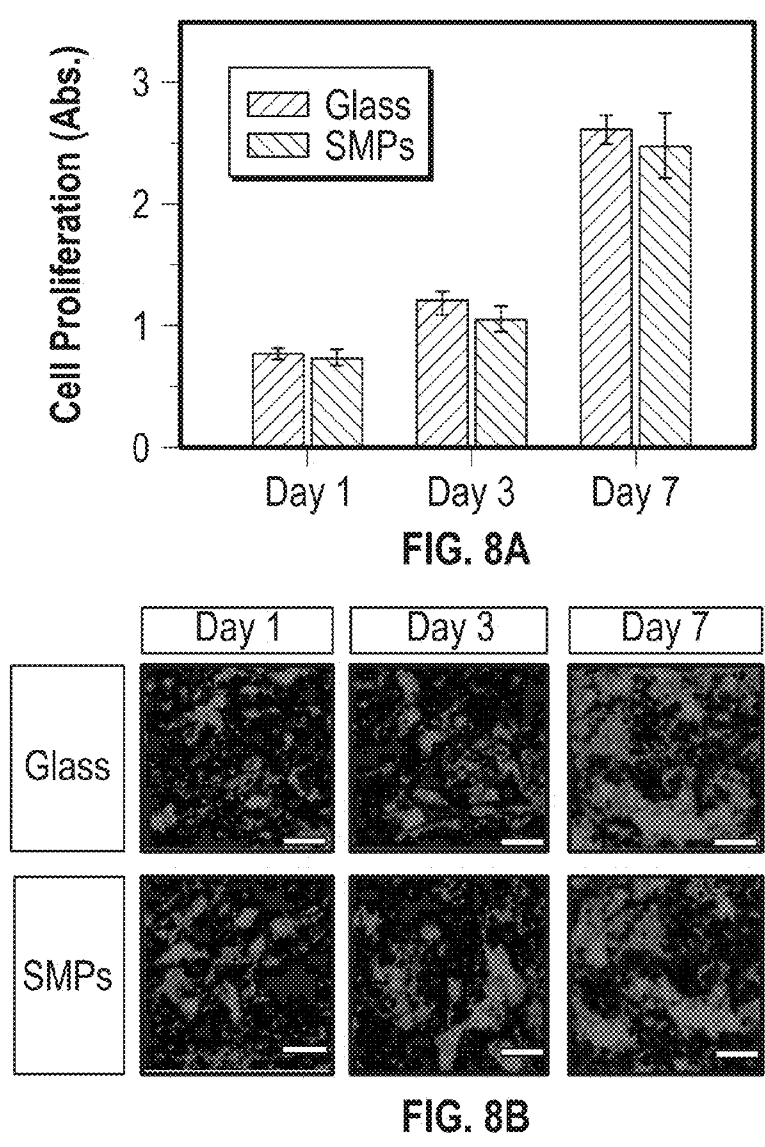
FIG. 8A illustrates the biocompatibility of the synthesized polymeric materials, and the NSC aggregation behavior NSC proliferation on SMP and glass samples after 1, 3, and 7 days of culture.
FIG. 8B illustrates the NSC morphology for SMP and glass samples after 1, 3 and 7 days of culture, where F-actin is colored red and nucleus is colored blue (Scale bar being 200 μm), and showing that there is no significant difference among these samples (N.S.), suggesting our SMPs exhibited an excellent cytocompatibility in vitro.
FIG. 8C illustrates 3D fluorescent image and image analysis of GFP-NSCs when cells seeded in the 4D micro-well arrays, with the 3D spectrum showing the fluorescent intensity distribution of aggregates when NSC grew in the micro-well arrays, and wherein the ortho (10/20) and (15/20) images demonstrated the aggregation morphology of NSCs at the different Z position of the micro-well arrays (Scale bar being 1 mm)

In order to evaluate the cytocompatibility of the sample SMPs, a standard cell viability and proliferation assay (CCK-8 assay) was performed which verified that the SMP substrate significantly sustained high cell survival after two weeks of culture as compared to the control glass substrates, as shown in FIG. 8A. Moreover, cell morphology was also investigated using F-actin staining. As shown in FIG. 8B, fluorescence images illustrated the NSCs growth on the SMP substrate was comparable with the glass substrate. There was no significant difference among these samples (N.S.), suggesting the exemplary SMPs exhibited an excellent cytocompatibility in vitro.

Having established that the SMP substrates could promote cell survival and growth, time-dependent neural development was explored along with the effect of 4D transformation on the neural differentiation of NSCs. To this end, the NSC aggregating behavior was investigated in the micro-well arrays in the first three days. After 3 days of culture, the aggregation of GFP-NSCs was studied by 3D confocal scanning which is illustrated in FIG. 8C. The images were further analyzed to better observe the aggregating features of NSCs. The 3D spectrum showed the fluorescent intensity distribution of aggregates when NSC grew in the micro-well arrays. After the 3D images were split into 20 slides of 2D images, the ortho (10/20) and (15/20) images demonstrated the aggregation morphology of NSCs at the different Z position of the micro-well arrays.

Figure 8D:
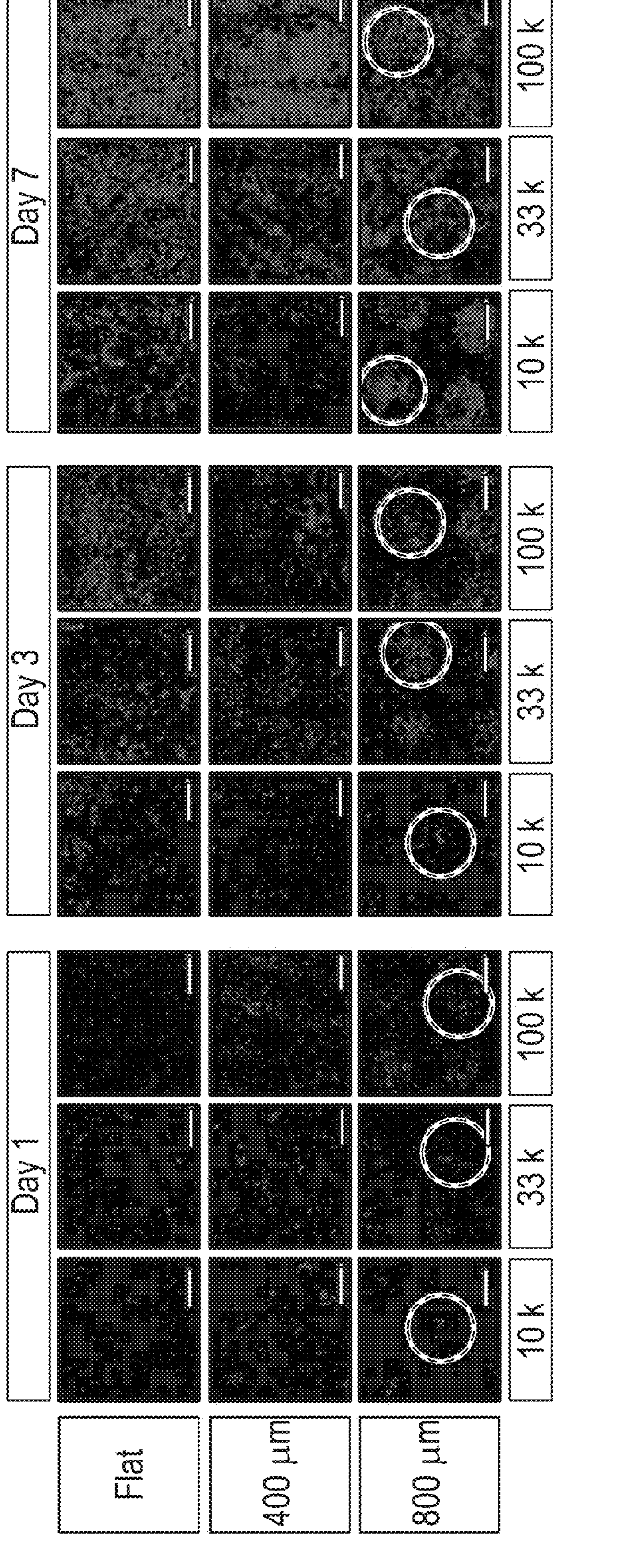
FIG. 8D depicts fluorescent images of NSCs with different cell densities on different culture substrates s (Flat, 400 μm, and 800 μm micro-wells) after 1, 3, and 7 days of culture, with the dotted circles indicating the NSC aggregation in the microwell region (Scale bar being 600 μm)

After that, the effect of cell number and micro-well size on the aggregating behaviors of NSCs was further explored. The micro-well arrays with two feature diameters (400 μm and 800 μm) were imprinted using SL-printed micro-pillar PMMA arrays, and a flat sample was served as control. The NSCs with different cell densities ($1\times10^4$, $3.3\times10^4$, $1\times10^5$ cells/mL) were seeded into patterned micro-wells and cultured to confluence after seven days of 4D transformation, in order to generate optimal size-controlled aggregation. The fluorescence images showed the formation of NSC aggregates on different culture substrates, illustrated in FIG. 8D. For instance, dotted circles indicate the NSC aggregation in the microwell region.

Figure 8E:
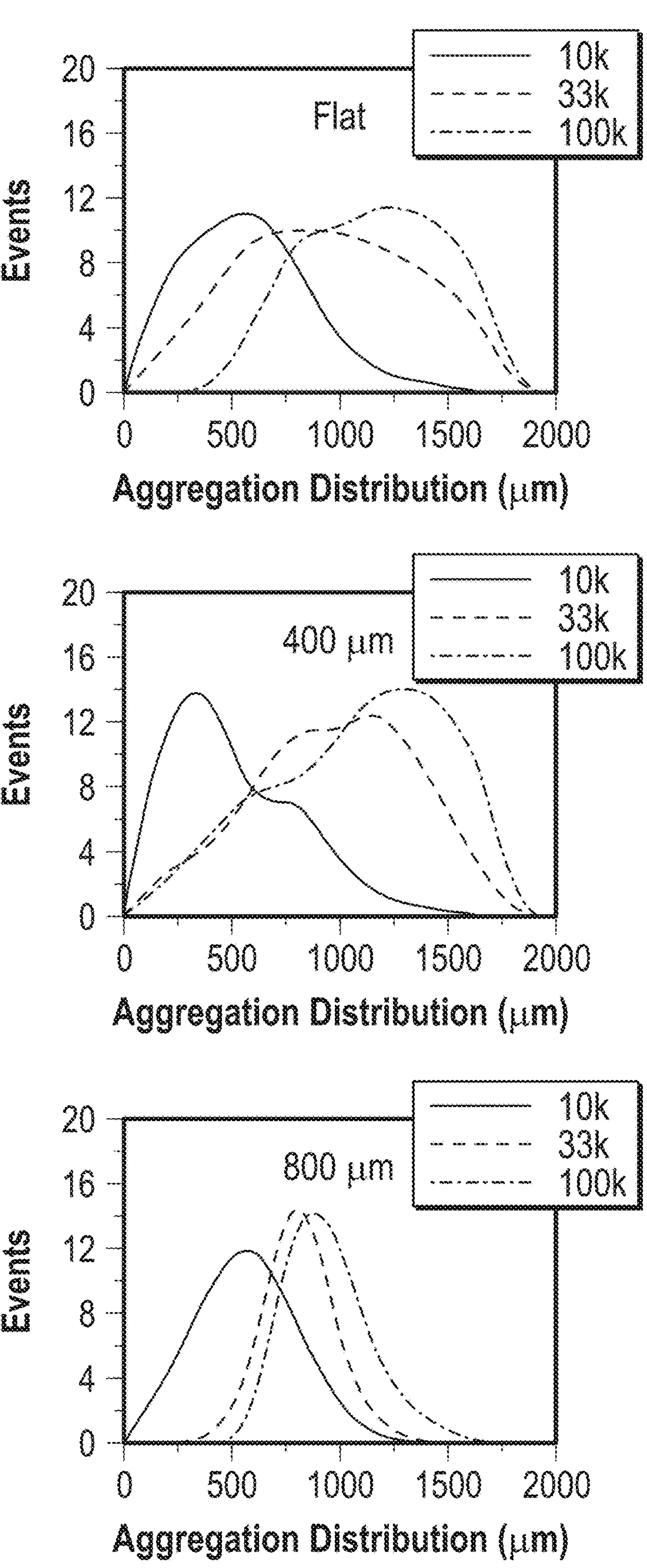
FIG. 8E illustrates quantitative analysis of NSC size distribution by fluorescence aggregation at 3 days.

The conventional aggregate formation on flat substrate resulted in a heterogeneous distribution of cell clumps with various sizes. The micro-wells with 400 μm (small size) at the first day showed a size-dependent cell distribution, but the NSC density in these small wells was unable to form perfect aggregates during the 4D transformation of the substrate. In contrast, the micro-wells with 800 μm (large size) generated uniform, compact NSC aggregates of controlled size based on micropatterning cell colonies at a defined diameter. Moreover, after seven days of culture, higher cell densities (both $3.3\times10^4$ and $1\times10^5$ cells/mL) exhibited excellent cell confluence or monolayers around loose aggregates. The quantitative analysis of NSC size distribution was also performed by fluorescence aggregation to determine the optimal cell seeding number at 3 day, shown in FIG. 8E.

Results showed that when cell density was higher than $3.3\times10^4$ cells/mL, uniform NSC aggregates were formed at three days, further continuing to the confluence at seven days. This typical process fully replicated the NSC behaviors (morphology and biological features) at different stages of in vitro neural differentiation. The data suggested that both cell density and micro-well size influenced NSC aggregation behaviors, which is expected to affect the following differentiation trajectories.

The specific response of neuronal cells to topographical cues can result in the axon guidance and the growth of transplanted neurons to enhanced therapeutic effects for nerve injury. Therefore, in order to precisely control the polarity and directional growth as well as influence the neuronal differentiation of NSCs, the aligned topographical feature was further created to direct the formation of highly aligned axons from the differentiating NSCs. The surface with micro- or nano-topographical patterns are able to control the NSC alignment and improve the neurogenesis.

Figures 9A, 9B:
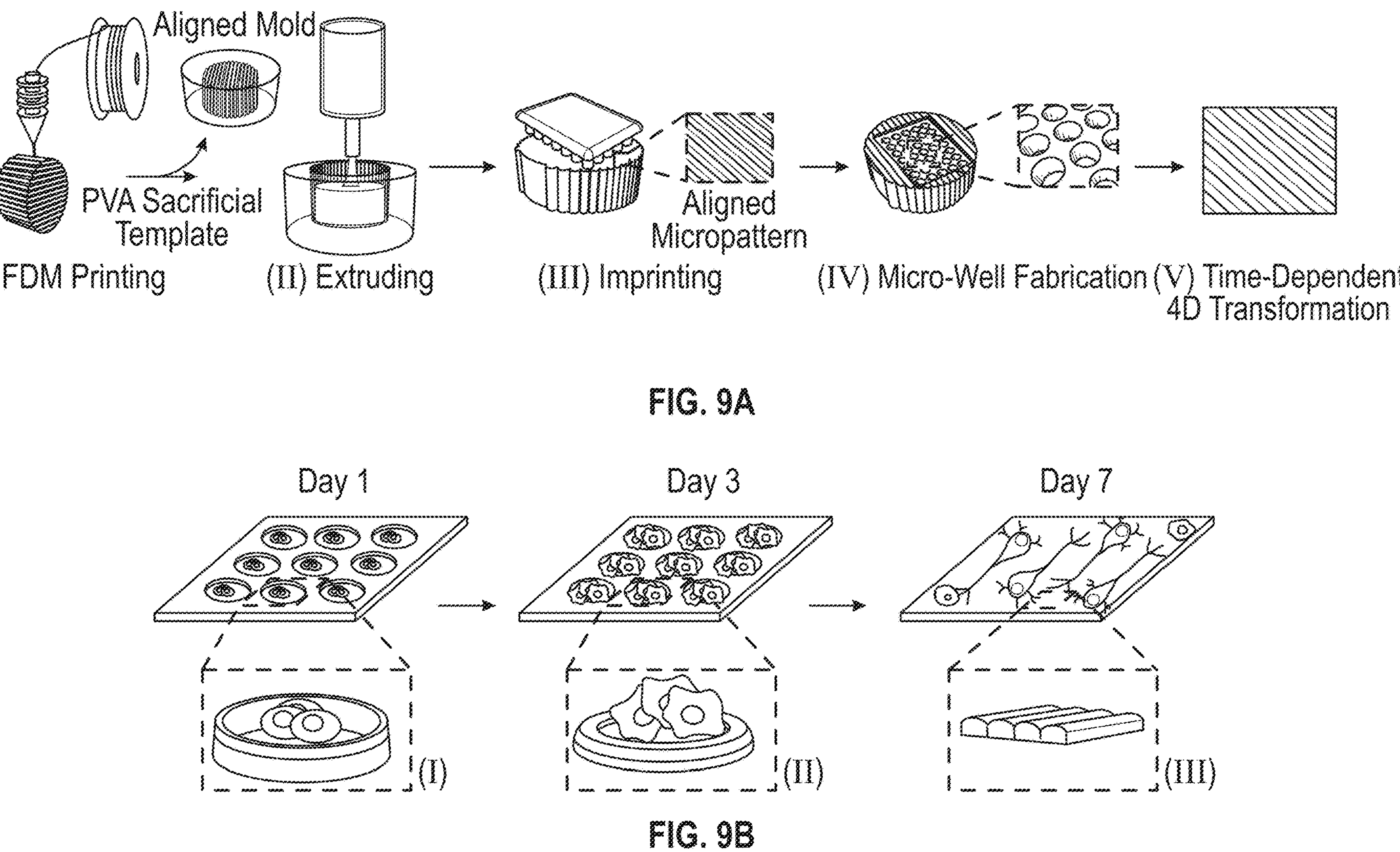
FIG. 9A illustrates fabrication and characterization of 4D aligned/micro-well arrays on SMPs, and in particular the fabrication of micro-well arrays and their time-dependent 4D transformation.
FIG. 9B illustrates time-dependent cell patterning process during 7 days of culture, including (I) Reprogrammed micro-well arrays and cell seeding at day 1, (II) 4D shape recovery and NSC aggregation at day 3, and (III) Original aligned patterns and axonal alignment of the differentiating NSCs at day 7.

As shown in FIG. 9A, a highly aligned micropattern with a width of 100 μm was prepared on the surface of the sample. Thus, a "key-lock copied" template strategy that incorporates 3D printed PVA sacrificial mold and PDMS microgrooves was performed to create aligned micropattern with a width of 100 μm, which was described in Method. After that, the micro-well arrays were created on the aligned micropatterned sample using the aforementioned "thermo-mechanical imprint" method. As illustrated in FIG. 9B, the resultant 4D culture substrate that integrated "temporary" micro-well arrays and "programmable" aligned patterns were used to cater the time-dependent differentiation behavior of NSCs. FIG. 9B illustrates the time-dependent cell patterning process during 7 days of culture, with part (I) showing reprogrammed micro-well arrays and cell seeding at day 1, part (II) showing 4D shape recovery and NSC aggregation at day 3, and part (III) showing original aligned patterns and axonal alignment of the differentiating NSCs at day 7.

Figures 9C, 9D:
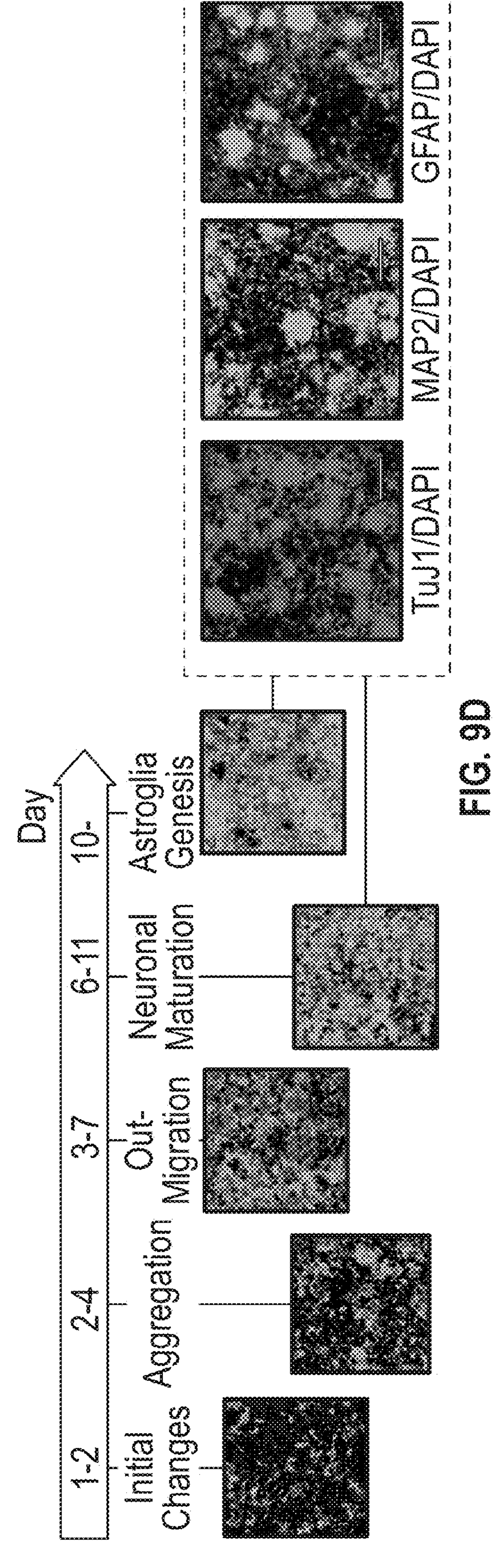
FIG. 9C illustrates optical images and 3D surface plots of 4D SMP substrates changing from micro-well arrays to aligned pattern (microgrooves) at 1, 3, and 7 days.
FIG. 9D illustrates time-dependent differentiation behavior of NSCs, demonstrating the different stages of retinoic acid (RA) induced in vitro neural differentiation of NSCs (microscopic images), and the biological features (the expression of neurogenic markers) in the differentiated NSCs. Neuronal marker: TuJ1, mature neuronal markers MAP2, and astrocytes marker GFAP.

As shown in FIG. 9C, the 4D transformation behavior of culture substrate with time was captured by optical microscopy, and 3D surface plots were created by the software. The images confirmed the surface pattern changing from "temporary" micro-well arrays to "programmable" aligned patterns.

The results herein demonstrate an engineered, favorable microenvironment for the NSC development, through the application of novel 4D culture substrates, which can specifically control the growth of NSC-derived neural tissue and axonal alignment for the development of more effective treatments for spinal cord injuries. FIG. 9D shows the different stages of RA induced in vitro neural differentiation of NSCs, and the biological features (the expression of neurogenic markers) in the differentiated NSCs. As mentioned above, NSCs tend to form aggregates at early differentiation while performing neurite extension and elongation in the late stage.

Figure 10A:
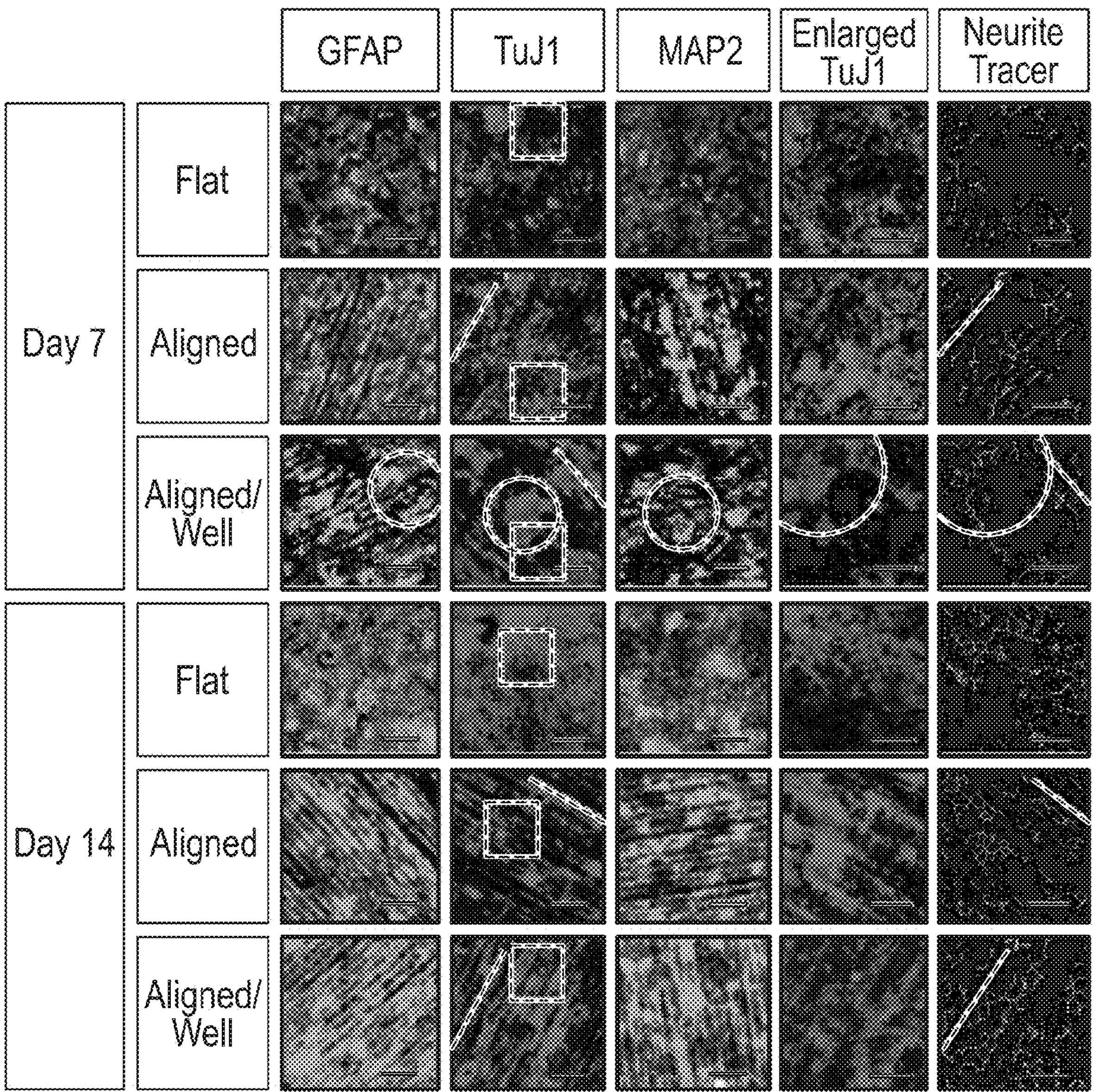
FIG. 10A NSC differentiation studies on 4D aligned/micro-well arrays on SMPs. Immunofluorescent images of NSC differentiation on 4D Aligned/micro-well arrays compared to flat samples and samples with aligned only, after culturing in differentiation medium for 2 weeks. GFAP and MAP2 are colored green, TuJ1 is colored red, and nuclei are colored blue. Scale bar is 500 μm. The dotted squares in TuJ1 images indicate the enlarged area, which is used to generate the images of neurite tracer (Scale bar is 200 μm). The dotted circles indicate the NSC aggregation in micro-well. The yellow dotted arrows show the direction of aligned patterns (microgrooves)

The results herein demonstrate that the 4D substrates are an excellent platform to enhance the differentiation of NSCs into neurons and glial cells, and further control axonal alignment of the differentiating NSCs. The immunostaining data illustrated in FIG. 10A demonstrate that the formed NSC aggregates were obviously out-migrated with well-array gradually disappearing after seven days of differentiation, and most of the aligned axons from the differentiated NSCs were identified by the expression of the neuronal marker TuJ1 on the 4D aligned/well-array substrates.

Figure 10B:
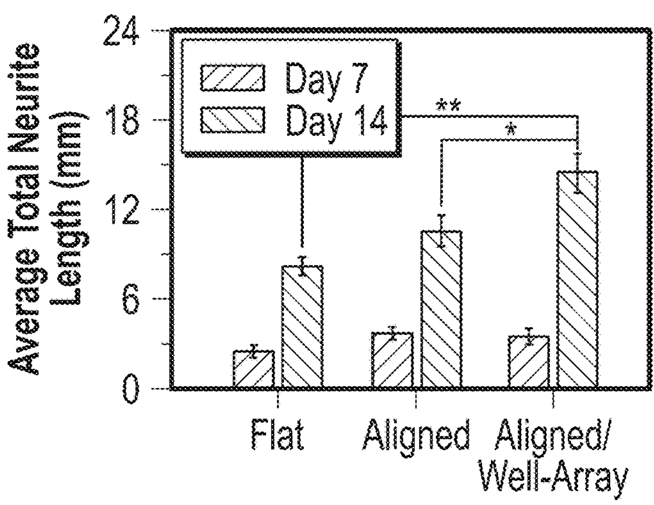
FIG. 10B illustrates the quantification of total neurite length of neural differentiation 4D aligned/micro-well arrays when compared to other corresponding groups at 7 days and 14 days (Data are mean±standard deviation; n=9; *p<0.05)

The presence of mature neuronal markers MAP2 and astrocytes marker GFAP were characterized to confirm neuronal maturation and astroglia genesis, respectively. Compared to flat and aligned substrates, higher expression of neuronal markers demonstrated that 4D aligned/well-array substrates accelerated the differentiation of NSCs. It is deduced that the well-arrays improved the formation of NSC aggregates, thus leading to an earlier neural differentiation. Especially, the significant interconnected neuronal aggregates and astroglia genesis were also observed after 14 days of culture. Moreover, the quantification of total neurite length of neural differentiation 4D aligned/micro-well arrays was also evaluated at 7 days and 14 days as illustrated in FIG. 10B.

Figure 10C:
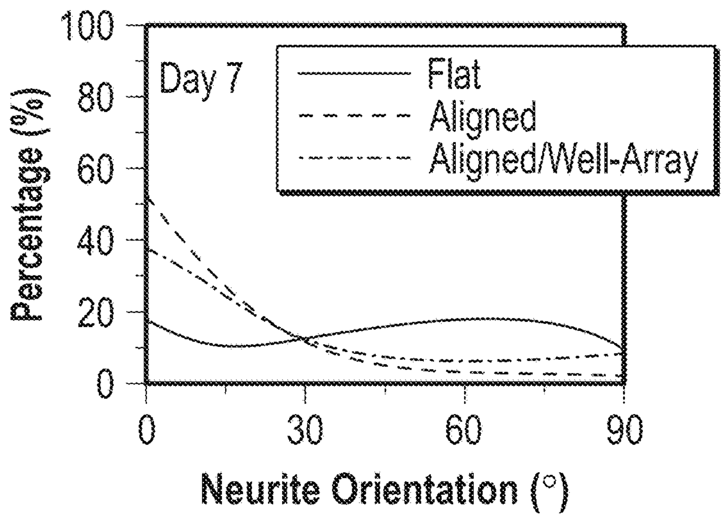
FIG. 10C illustrates the neurite direction of the microgrooves which were set as an angle of 0° (horizontal direction was set as 0° for the flat control samples), where the neurite major axis with respect to the direction of the microgrooves (or horizontal direction for flat control) was defined as the neurite orientation, and where the neurites were considered to be aligned if their angles fell into ±20° from the original benchmark.
Figure 10C:
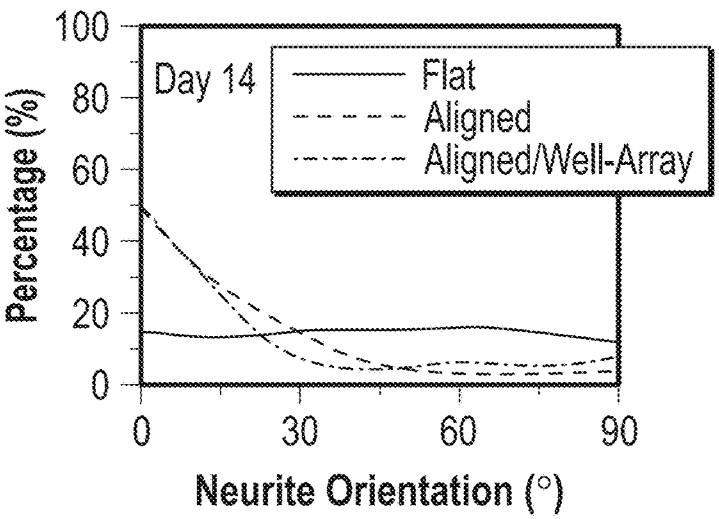

The aligned/micro-well arrays exhibited the highest neurite length when compared to other groups. As shown in FIG. 10C, after two weeks of differentiation, with aligned patterns recovering, it was observed that the differentiating NSCs showed the excellent alignment of axons on the 4D aligned/well-array substrates. In FIG. 10C, the neurite direction of the microgrooves was set as an angle of 0° (horizontal direction was set as 0° for the flat control samples). The neurite major axis with respect to the direction of the microgrooves (or horizontal direction for flat control) was defined as the neurite orientation. The neurites were considered to be aligned if their angles fell into ±20° from the original benchmark. The Results demonstrated that the engineered microenvironment consisting of 4D dynamic transformation and micro-topographical feature provides instructive physical cues that lead to enhanced neural differentiation of NSCs along with significant axonal alignment.

Next, to quantify the expression levels of these neuronal markers, we further performed rt-qPCR analyses of neural differentiation of NSCs on 4D aligned/well-array substrates and compared them to NSCs differentiated on only aligned, Flat and TCP substrates. Generally, with time increasing, gene expression of TuJ-1, MAP2, and GFAP from differentiating NSCs increased, whereas the undifferentiated NSC marker Nestin decreased for all culture substrates. The expression levels of neuronal and axonal markers were up-regulated on aligned and 4D aligned/well-array substrates compared to the control TCP and flat substrates.

Figure 11:
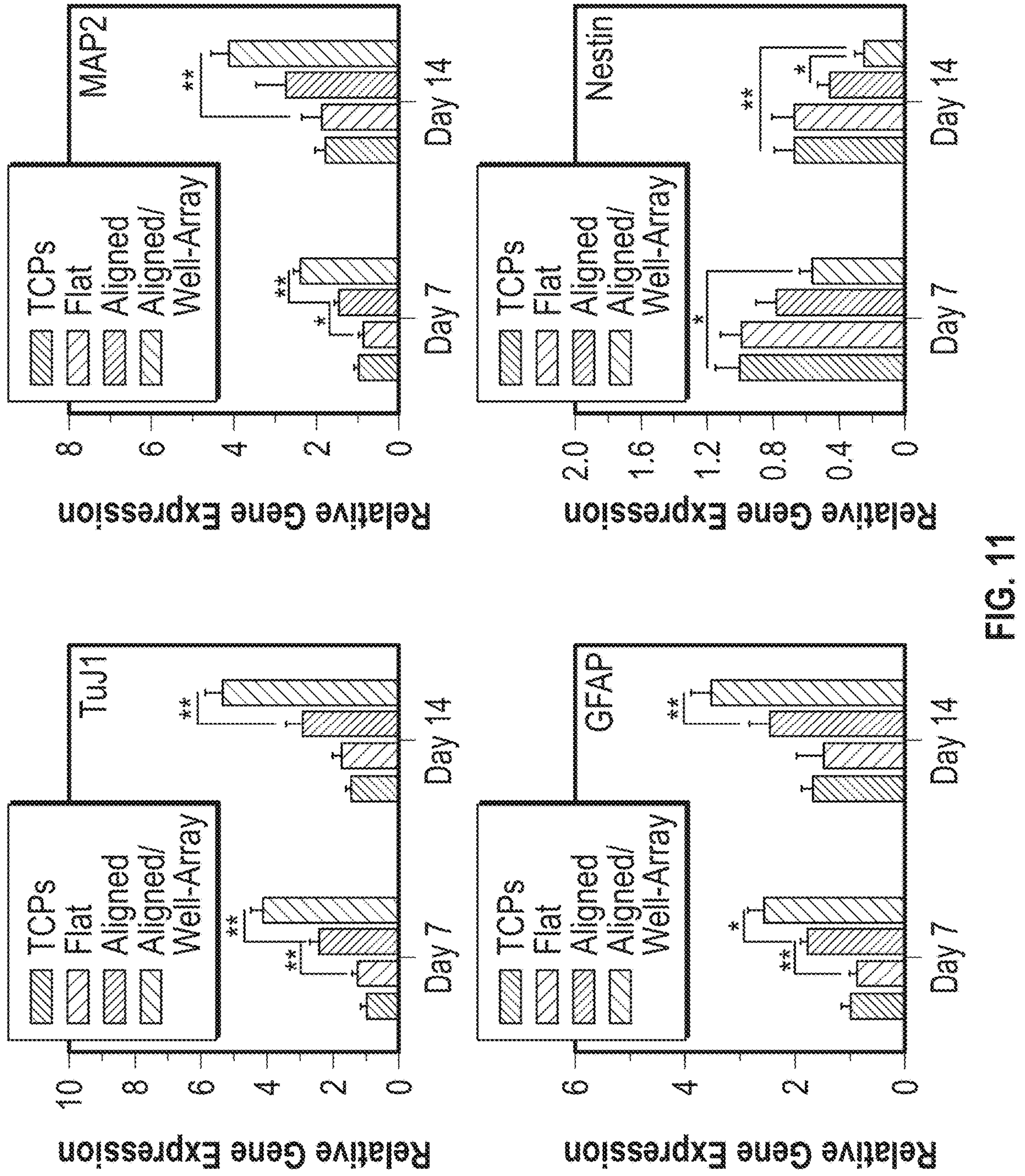
FIG. 11 illustrates gene expressions of NSCs on 4D aligned/micro-well arrays when compared to TCPs, Flat samples, and samples with aligned only for 2 weeks of culture, and wherein the data was normalized to the expression levels of cells on TCPs (Data are reported as mean±standard deviation, n=6, *P<0.05, **P<0.01).

Moreover, FIG. 11 demonstrates that the differentiation of NSCs on 4D aligned/well-array substrates showed the highest expression levels for neuronal markers (TuJ1 and MAP2) and astrocyte marker (GFAP). From this, it is concluded that the combined effect of having a microwell and aligned pattern on a single substrate shows significantly enhanced neural differentiation and remarkable alignment of differentiated NSCs. Therefore, it is demonstrated the dynamic 4D effect may better mimic the special growth microenvironments of neural tissue, and provide a potential method for catering different development stages of NSCs, thus hastening the functional recovery of injured neural tissues.

The following methods were employed in the present examples for the preparation and evaluation of samples.

Fabrication of NSC Programmable Culture Matrices (Culture Substrates)

In the above Examples, three printing techniques, including fused deposition modeling (FDM), extrusion, and UV LCD stereolithography (SLA), were used to fabricate the programmable culture matrices. First, a cylinder sacrificial mold with a diameter 12 mm and height 8 mm was designed with the software Autodesk123D (Autodesk Inc, CA, USA), and the stl. format file was then loaded into the software Slic3r which licensed under the GNU Affero General Public License, version 3. The infill density, the printing speed, and the layer height were assigned in Slic3r. The pre-designed structures were then printed via a Solidoodle® 3D FDM printer platform with a nozzle size of 100 μm. Open source software (Prontrface®) was employed to control the three stepper motors with an effective resolution of 100 μm in the x- and y-axis, and a minimum layer height of 50 μm in the z-axis. Polyvinyl alcohol (PVA) filament for 3D printing was obtained from Matter Hackers (Orange County, Califormia). Polyvinyl alcohol filament, with a diameter of 1.75 mm, was used as the sacrificial mold material, and the printing temperature was set at 190° C. The PVA sacrificial mold was printed with a layer height of 100 μm to generate the aligned surface structure. The mold was then coated with PDMS and cure at 70° C. for two hours in order to obtain PDMS microgrooves with a width of 100 Next, preset amount of the 4D ink materials was then extruded into the PDMS mold, and then performed a curing process as described above.

After cooled to room temperature, the aligned micropatterned scaffolds were taken out and ready for other operations.

Finally, micro-wells were fabricated on our flat and aligned scaffold to improve the NSC spheroid formation at an early stage of neural development. A cubic mold 9 mm (L)×6 mm (W)×2 mm (H) with micro-pillars (800 μm and 400 μm in diameter) was designed with the software Autodesk 123D (Autodesk Inc, CA, USA), and saved as a stl. format file. The models were uploaded into desktop SLA printer to slice the digital model into layers for printing. Two different diameters of micro-pillar templates, 800 μm and 400 μm, were printed with poly(methyl methacrylate) (PMMA) resin for the fabrication of hard molds. The speed of operation is 25 mm/h, the XY resolution is 50×50 and the layer height is 50 μm. After the printing, a thermomechanical reprogramming process was performed to create the temporary micro-wells on the 4D scaffolds as follows: the 4D scaffolds were imprinted by micro-pillar mold with a clamp at 60° C. for 10 min, and then moved to ice water for 10 min.

Cell Culture, Proliferation, and Morphology.

NSCs in the present examples were cloned from mouse neuroectoderm (NE-4C) and were purchased from American Type Culture Collection (ATCC). NSCs (passage No. 3-6) were cultured in Eagle's minimum essential medium (ATCC) supplemented with 5% fetal bovine serum (FBS), 1% (v/v) L-glutamine, and 1% penicillin/streptomycin solution, under standard cell culture conditions (37° C., a humidified, 5% CO2/95% air environment). NSCs were seeded on glasses and SMPs at a density of $5\times10^4$ cells/mL and continuously cultured for 1, 3, and 7 days. At the predetermined time interval, the culture medium containing 10% CCK-8 solution (Dojindo, Japan) was added and incubated for 2 h. 200 μL of the medium was transferred into a 96-well plate, and the absorbance at a wavelength of 450 nm was quantified by a spectrophotometer (Thermo, USA). The NSC morphology was evaluated by F-actin staining. At each predetermined time, all samples were fixed with 10% formalin for 15 min and then permeabilized with 0.2% Triton-100 for 10 min. The samples were then stained with a Texas Red-X phalloidin solution (1:100) to stain the cells' cytoskeleton for 30 min, followed by 4',6-diamidino-2-phenylindole (DAPI) (1:1,000) solution to stain the cells' nuclei for another 5 min. The images were observed using laser confocal microscopy (Carl Zeiss LSM 710).

Cell Aggregation Evaluation Staining

In the cell aggregation evaluation of the examples above, the green fluorescent protein transfected NSCs (GFP-NSCs, NE-GFP-4C, ATCC) were seeded on the micro-well arrays of 4D substrate at a density of $5\times10^4$ cells/mL and cultured for 3 days. The 3D fluorescent images were taken by confocal microscopy and analyzed by Zen software (Zeiss). Additionally, in order to optimize the formation of NSC spheroids, NSCs were seeded on the scaffolds at different densities of $1\times10^4$, $3.3\times10^4$, $1\times10^5$ cells/cm$^2$, and cultured for 7 days under standard cell culture conditions. At each predetermined time, the cells were fixed with 10% formalin for 15 min and permeabilized in 0.1% Triton X-100 for 10 min. The cells were stained with Texas red fluorescent dye for 30 min and then DAPI blue fluorescent dye for 5 min to observe NSC aggregation on the scaffolds. The double-stained samples were imaged on the confocal microscope. The aggregation distribution of NSCs at 3 days was quantified by Image J analysis software (National Institutes of Health). Six visible areas were randomly selected for quantifying statistical analysis on each sample; there were five samples in each group.

Neurogenic Differentiation.

In the Examples above, the neurogenic differentiation of NSCs was performed by seeding NSCs on the various scaffolds at $3\times10^4$ cells/cm$^2$ and maintained in the growth medium for 24 hours. To induce the neurogenic differentiation, the samples were cultured in the neurogenic medium which consisted of the growth medium supplemented $10^{-6}$ M RA, and the medium was exchanged every other day.

Immunofluorescence staining.

Neurogenic differentiation of NSCs in the Examples herein was identified using an immunofluorescence staining. After incubation with neurogenic differentiation medium for 7 and 14 days, the cells were fixed with 10% formalin for 15 min, treated with 0.1% Triton X-100 for 10 min. Then the samples were incubated with a blocking solution (containing 1% bovine serum albumin (BSA), 0.1% Tween 20 and 0.3 M glycine in PBS) for 2 h. The first primary antibodies of mouse anti-TuJ1 (1:1,000), rabbit anti-GFAP antibody (1:500) and rabbit anti-MAP2 antibody (1:500) were gently mixed with samples overnight at 4° C. Next, the secondary antibodies of goat anti-mouse Alexa Fluor 594 (1:1,000) and goat anti-rabbit Alexa Fluor 488 (1:1,000) were incubated with samples in the dark for 2 h at room temperature, followed by DAPI (1:1,000) solution incubation for 5 min. The immunofluorescence images were taken using confocal microscopy. Average total neurite length and orientation were quantified by Image J analysis software (NeuriteTracer). Three visible areas were randomly selected for quantifying statistical analysis on each sample; there were three samples in each group. The direction of the microgrooves was set as an angle of 0° (horizontal direction was set as 0° for the flat control samples). The neurite major axis with respect to the direction of the microgrooves (or horizontal direction for flat control) was defined as the neurite orientation. The neurites were considered to be aligned if their angles fell into ±20o from the original benchmark.

Real-Time Quantitative Polymerase Chain Reaction (Rt-qPCR).

The neurogenic gene expression of all samples in the Examples herein, including neuron-specific class III β-tubulin (TuJ1), microtubule-associated protein 2 (MAP2), glial fibrillary acidic protein (GFAP), and Nestin, were analyzed by the rt-qPCR assay. Briefly, the total RNA content was extracted from the samples using Trizol reagent (Life Technologies). The RNA quality and concentration were determined from the absorbance at 260 and 280 nm with a microplate reader. RNA samples were reverse-transcribed to cDNA using a Prime Script™ RT reagent Kit (TaKaRa). RT-PCR was then performed on a CFX384 Real-Time System (BIORAD) by using SYBR Premix Ex Taq™ (TaKaRa) according to the manufacturer's protocol. The gene expression level of target genes was normalized against the housekeeping gene glyceraldehyde 3-phosphate dehydrogenase (GAPDH). The relative gene expression of the samples was normalized against the control group to obtain relative gene expression fold values and calculated via the 2-delta delta (2-ΔΔCt) cycle-threshold method.

```
Primer sequences are as follows:
TUJ1, forward primer
5'-AGCTGTTCAAACGCATCTCG-3' and

reverse primer
5'-GACACCAGGTCATTCATGTTGC-3';

MAP2, forward primer
5'-TTCTCCACTGTGGCTGTTTG-3' and

reverse primer
5'-GAGCCTGTTTGTAGACTGGAAGA-3';

GFAP, forward primer
5'-CCTTCCTTCCCTGGTTTTCT-3' and

reverse primer
5'-TGCTCATCTTTCCTCTTCCC-3';

Nestin, forward primer
5'-GTGGCCTCTGGGATGATG-3' and

reverse primer
5'-TTGACCTTCCTCCCCCTC-3';

GAPDH, forward primer
5'-GTGGCCTCTGGGATGATG-3' and

reverse primer
5'-ACTCCTCAGCAACTGAGGG-3'.
```

Statistical Analysis.

The mean and standard deviation was plotted for each sample group (n=6). Then, a one-way analysis of variance (ANOVA) ($p<0.05$) with a post-hoc Tukey Honestly Significant Difference test was performed on each set of data. The statistical significance was indicated with an asterisk. That is, samples connected with an asterisk were significantly different.

What is claimed is:

1. A substrate for cell growth comprising a shape memory polymer having a first topographical shape, said shape memory polymer configured for transformation from the first topographical shape to a predetermined second topographical shape during a predetermined time period in response to a stimulus, each of the first topographical shape and the second topographical shape comprising exposed portions of the substrate.

2. The substrate of claim 1, wherein the shape memory polymer comprises a combination of a monomer, a crosslinker and a crosslinking modulator.

3. The substrate of claim 2, wherein the monomer is a bisphenol epoxides, the crosslinker is a polyether with terminal amine functional groups and the crosslinking modulator is an alkyl amine.

4. The substrate of claim 2, wherein the monomer is bisphenol A diglycidyl ether, the crosslinker is poly(propylene glycol) bis(2-aminopropyl) ether and the crosslinking modulator is decylamine.

5. The substrate of claim 1, wherein the first topographical shape comprises micro-wells and the second topographical shape comprises microgrooves.

6. The substrate of claim 1, wherein the substrate is printed via 4D printing, and wherein the 4D printed substrate was initially printed with the second topographical shape, but was transformed to the first topographical shape by imprinting.

7. The substrate of claim 1, wherein the stimulus is a change in temperature.

8. A system for cell growth comprising a 4D printed culture substrate comprising a shape memory polymer that is configured for transformation from a first topographical shape to a second topographical shape during a predetermined time period in response to a stimulus.

9. The system of claim 8, wherein the shape memory polymer comprises a combination of a monomer, a crosslinker and a crosslinking modulator.

10. The system of claim 9, wherein the monomer is a bisphenol epoxides, the crosslinker is a polyether with terminal amine functional groups and the crosslinking modulator is an alkyl amine.

11. The system of claim 9, wherein the monomer is bisphenol A diglycidyl ether, the crosslinker is poly(propylene glycol) bis(2-aminopropyl) ether and the crosslinking modulator is decylamine.

12. The system of claim 8, wherein the first topographical shape is comprised of micro-wells and the second topographical shape is comprised of microgrooves.

13. The system of claim 8, wherein the stimulus is a change in temperature.

14. The system of claim 13, wherein the change in temperature is from 23° C. to 37° C.

15. The system of claim 8, further comprising neural stem cells growing on the 4D printed culture substrate.

16. A method of producing a 4D printed culture substrate system comprising:

fabricating a 4D printed culture substrate via extrusion to form a second topographical shape of the 4D printed culture substrate; and thermomechanical reprogramming of the 4D printed culture substrate to form the first topographical shape of the 4D printed culture substrate.

17. The method of claim 16, wherein the fabrication of the 4D printed culture substrate comprises the steps of:

extruding the shape material polymer into a mold with micro-grooves having a width between 10 μm to 200 μm; and curing the prepared 4D material within the mold.

18. The method of claim 16, wherein the thermomechanical reprogramming of the 4D printed culture substrate comprises the steps of:

imprinting the 4D printed culture substrate with a micro-pillar mold with micro-pillars having a diameter between 200 μm to 1 mm; and maintaining the 4D printed culture substrate at about 20° C. to 25° C. to fix the first topographical shape of the 4D printed culture substrate.

19. A method of using a 4D printed culture substrate system comprising:

obtaining a 4D printed culture substrate system having a first topographical shape comprising of micro-wells which is maintained at from about 23° C. to 25° C.; and culturing cells on the micro-wells of the 4D printed culture substrate system under standard cell culture conditions, wherein the 4D printed culture substrate undergoes a transformation of topographical shape during the said period from micro-wells to micro-grooves.

20. The method of claim 19, wherein the cells are adherent stem cells.

* * * * *